US009693971B2

(12) United States Patent
Stumpff et al.

(10) Patent No.: US 9,693,971 B2
(45) Date of Patent: Jul. 4, 2017

(54) COMPOSITIONS FOR ALLEVIATING GASTROINTESTINAL TRACT DISORDERS OR ASSOCIATED SYSTEMIC DISORDERS IN RUMINANTS AND CAMELIDS

(71) Applicant: FREIE UNIVERSITÄT BERLIN, Berlin (DE)

(72) Inventors: Friederike Stumpff, Berlin (DE); Julia Rosendahl, Berlin (DE); Jörg Aschenbach, Leipzig (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 0 days.

(21) Appl. No.: 14/418,405

(22) PCT Filed: Jul. 31, 2013

(86) PCT No.: PCT/EP2013/066094
§ 371 (c)(1),
(2) Date: Jan. 29, 2015

(87) PCT Pub. No.: WO2014/020067
PCT Pub. Date: Feb. 6, 2014

(65) Prior Publication Data
US 2015/0164822 A1    Jun. 18, 2015

(30) Foreign Application Priority Data

Jul. 31, 2012 (DE) ........................ 10 2012 015 029

(51) Int. Cl.
| | |
|---|---|
| *A61K 31/045* | (2006.01) |
| *A61K 31/05* | (2006.01) |
| *A23K 20/105* | (2016.01) |
| *A23K 20/111* | (2016.01) |
| *A23K 20/10* | (2016.01) |
| *A23K 50/10* | (2016.01) |
| *A61K 9/00* | (2006.01) |

(52) U.S. Cl.
CPC .............. *A61K 31/05* (2013.01); *A23K 20/10* (2016.05); *A23K 20/105* (2016.05); *A23K 20/111* (2016.05); *A23K 50/10* (2016.05); *A61K 31/045* (2013.01); *A61K 9/0056* (2013.01)

(58) Field of Classification Search
CPC .................................................. A61K 31/045
See application file for complete search history.

(56) References Cited

U.S. PATENT DOCUMENTS

2010/0330187 A1* 12/2010 Bravo ..................... A23K 1/005
424/490

FOREIGN PATENT DOCUMENTS

| EP | 1 609 372 A2 | 12/2005 |
|---|---|---|
| EP | 2 042 041 A2 | 4/2009 |
| EP | 2 368 440 A1 | 9/2011 |
| WO | 2011/153299 A2 | 12/2011 |

OTHER PUBLICATIONS

Ramsey, S. "An Introduction to TRP Channels." Annu. Rev. Physiol. (2006), vol. 68, pp. 619-647, IDS of Jun. 2, 2015.*
McDonald et al., "The Absorption of Ammonia from the Rumen of the Sheep", Biochemical Journal, vol. 42, Issue 4, 1948, pp. 584-587.
Möller., "Luftverschmutzung durch Industrie, Landwirtschaft und Haushalte", Bundeszentrale für politische Bildung (bpb), Mar. 30, 2009, pp. 4 (English Abstract).
Nagaraja et al., "Effect of ionophore antibiotics on experimentally induced lactic acidosis in cattle", American Journal of Veterinary Research, vol. 46, Issue 12, Dec. 1985, pp. 2444-2452.
Nilius et al., "TRPV4 calcium entry channel: a paradigm for gating diversity", American Journal of Physiology—Cell Physiology, vol. 286, Issue 2, Feb. 2004, pp. C195-C205.
Nocek et al., "Bovine Acidosis: Implications on Laminitis", Journal of Dairy Science, vol. 80, Issue 5, May 1997, pp. 1005-1028.
Nordlund et al., "Herd-Based Diagnosis of Subacute Ruminal Acidosis", Preconvention Seminar 7: Dairy Herd Problem Investigation Strategies, 36th Annual Conference, Sep. 15-17, 2003, pp. 1-6.
Owens et al., "Acidosis in cattle: a review", Journal of Animal Science, vol. 76, Issue 1, Jan. 1998, pp. 275-286.
Owsianik et al., "Permeation and Selectivity of TRP Channels", Annual Review of Physiology, vol. 68, Mar. 2006, pp. 685-717.
Owsianik et al., "The transient receptor potential family of ion channels", Genome Biology, vol. 12, Issue 3, 2011, pp. 1-11.
Radostits et al., "Veterinary Medicine: A Textbook of the Diseases of Cattle, Sheep, Pigs, Goats and Horses", 2000, pp. 1420-1435.
Ramsey et al., "An Introduction to TRP Channels", Annual Review of Physiology, vol. 68, Mar. 2006, pp. 619-647.
Re'mond et al., "Partitioning of nutrient net fluxes across the portal-drained viscera in sheep fed twice daily: effect of dietary protein degradability", British Journal of Nutrition, vol. 102, Issue 3, Aug. 2009, pp. 370-381.
Schoeber et al., "RGS2 Inhibits the Epithelial Ca2 Channel TRPV6", The Journal of Biological Chemistry, vol. 281, Issue 40, Oct. 6, 2006, pp. 29669-29674.
Schweigel et al., "Mg2+ transport in sheep rumen epithelium: evidence for an electrodiffusive uptake mechanism", American Journal of Physiology—Gastrointestinal and Liver Physiology, vol. 277, Issue 5, Nov. 1, 1999, pp. G976-G982.
Schweigel et al., "Rumen epithelial cells adapt magnesium transport to high and low extracellular magnesium conditions", Magnesium Research, vol. 22, Issue 3, 2009, pp. 133-150.

(Continued)

*Primary Examiner* — Noble Jarrell
*Assistant Examiner* — John S Kenyon
(74) *Attorney, Agent, or Firm* — Maschoff Brennan

(57) ABSTRACT

Provided are feed supplements for the alleviation of gastrointestinal tract disorders and associated systemic disorders in ruminants, methods for producing feed supplements and feeds and feed additives containing such feed supplements. Furthermore, medicaments for the treatment of diseases which are associated with disorders of the gastrointestinal tract, particularly rumen acidosis and parturient paresis, are specified.

12 Claims, 10 Drawing Sheets

(56) References Cited

OTHER PUBLICATIONS

Smith et al., "Bisandrographolide from Andrographis paniculata Activates TRPV4 Channels", Journal of Biological Chemistry, vol. 281, No. 40, Oct. 6, 2006, pp. 29897-29904.
Steinwidder et al., "Milchviehfütterung: Tier- und leistungsgerecht", Aug. 1, 2005, pp. 240 (English Abstract).
Stock et al., "G91-1047 Acidosis", NebGuide—Historical Materials from University of Nebraska—Lincoln Extension—Paper 198, Jan. 1, 1991, pp. 8.
Strecker., "Untersuchungen zur pH-Regulation am Blättermagenepithel des Schafes mit H+-sensitiven Mikroelektroden", Dissertation, Freie Universität Berlin, 2011, pp. 1-178.
Stumpff et al., "Arole for Magnesium in the Regulation of Ruminal Sodium Transport", Focus on Signal Transduction Research, 2006, pp. 1-30.
Stumpff et al., "Characterization of Maxi-K-Channels in Bovine Trabecular Meshwork and Their Activation by Cyclic Guanosine Monophosphate", Investigative Ophthalmology & Visual Science, vol. 38, Issue 9, Aug. 1997, pp. 1883-1892.
Stumpff et al., "Cultured ruminal epithelial cells express a large-conductance channel permeable to chloride, bicarbonate, and acetate", Pflügers Archiv—European Journal of Physiology, vol. 457, Issue 5, Mar. 2009, pp. 1003-1022.
Stumpff et al., "Effects of the Bacillus thuringiensis Toxin Cry1Ab on Membrane Currents of Isolated Cells of the Ruminal Epithelium", Journal of Membrane Biology, vol. 219, Issue 1-3, Oct. 2007, pp. 37-47.
Stumpff et al., "Ionic Conductances of the Ruminal Epithelium", Dissertation, Freien Universität Berlin, 2011, pp. 1-141.
Stumpff et al., "Sheep rumen and omasum primary cultures and source epithelia: barrier function aligns with expression of tight junction proteins", The Journal of Experimental Biology, vol. 214, Sep. 1, 2011, pp. 2871-2882.
Stumpff et al., "Stimulation of cannabinoid (CB1) and prostanoid (EP2) receptors opens BKCa channels and relaxes ocular trabecular meshwork", Experimental Eye Research, vol. 80, Issue 5, May 2005, pp. 697-708.
Stumpff et al., "Stimulation of Maxi-K Channels in Trabecular Meshwork by Tyrosine Kinase Inhibitors," Investigative Ophthalmology & Visual Science, vol. 40, Issue 7, Jun. 1999, pp. 1404-1417.
Thorniley et al., "A single drench of virginiamycin to control acidosis in sheep and cattle", Proceedings Australian Society of Animal Production, vol. 21, 1996, pp. 243-246.
Vanhatalo et al., "Effects of feeding grass or red clover silage cut at two maturity stages in dairy cows. 1. Nitrogen metabolism and supply of amino acids", Journal of Dairy Science vol. 92, Issue 11, Nov. 2009, pp. 5620-5633.
Vriens et al., "Herbal Compounds and Toxins Modulating TRP Channels", Current Neuropharmacology, vol. 6, Issue 1, Mar. 2008, pp. 79-96.
Xu et al., Oregano, thyme and clove-derived flavors and skin sensitizers activate specific TRP channels, Nature Neuroscience, vol. 9, Issue 5, May 2006, pp. 628-635.
"Animal Health Transition Cow Health", Journal of Animal Science vol. 80, Supplement 1/Journal of Dairy Science, vol. 85, Supplement 1, 2002, pp. 189-192.
"High Performance Ammonia Gas Sensing Electrode", Thermo Scientific Orion 9512HPBNWP, pp. 2, 2007.
Abdoun et al., "Ammonia and urea transport across the rumen epithelium: a review", Animal Health Research Reviews, vol. 7, Issue 1-2, 2006, pp. 43-59.
Abdoun et al., "Modulation of electroneutral Na transport in sheep rumen epithelium by luminal ammonia", American Journal of Physiology—Gastrointestinal and Liver Physiology, vol. 289, Issue 3, 2005, pp. G508-G520.
Abdoun et al., "Modulation of urea transport across sheep rumen epithelium in vitro by SCFA and CO2", American Journal of Physiology—Gastrointestinal and Liver Physiology, vol. 298, Issue 2, Feb. 2010, pp. G190-G202.

Agarwal et al., "Effect of peppermint (*Mentha piperita*) oil on in vitro methanogenesis and fermentation of feed with buffalo rumen liquor", Animal Feed Science and Technology, vol. 148, Issue 2-4, Jan. 16, 2009, pp. 321-327.
Ando et al., "Effect of peppermint feeding on the digestibility, ruminal fermentation and protozoa", Livestock Production Science, vol. 82, Issue 2-3, Aug. 2003, pp. 245-248.
Aperce, C. C., "Factors Influencing *Escherichia coli* O157 Colonization of the Gastrointestinal Tract of Feedlot Cattle", Ph.D Dissertation, 2012, pp. 166.
Armstrong, R. B., "Mechanisms of exercise-induced delayed onset muscular soreness: a brief review", Medicine and Science in Sports and Exercise, vol. 16, Issue 6, Dec. 1984, pp. 529-538.
Campeneere et al., Feeding measures to reduce nitrogen excretion in dairy cattle, Archives of Animal Nutrition, vol. 63, Issue 2, Apr. 6, 2009, pp. 87-103.
Castillejos et al., "Effect of Essential Oil Active Compounds on Rumen Microbial Fermentation and Nutrient Flow in In Vitro Systems", Journal of Dairy Science, vol. 89, Issue 7, Jul. 2006, pp. 2649-2658.
Coe et al., "Effect of virginiamycin on ruminal fermentation in cattle during adaptation to a high concentrate diet and during an induced acidosis", Journal of Animal Science, vol. 77, No. 8, 1999, pp. 2259-2268.
Coffman et al., "The Use of Drugs in Food Animals: Benefits and Risks", National Academy of Sciences, 1999, pp. 276.
Cook et al., "Modern techniques for monitoring high-producing dairy cows 2. Practical applications", In Practice, vol. 28, 2006, pp. 598-603.
Crookenden et al., "Source of metabolizable energy affects gene transcription in metabolic pathways in adipose and liver tissue of nonlactating, pregnant dairy cows", Journal of Animal Science, vol. 82, Issue 11, Nov. 1999, pp. 2486-2496.
Dirksen., "Fütterungs-, stoffwechsel-,mangel- und vergiftungsbedingte Krankheiten mit Beteiligung mehrerer Organsysteme", Innere Medizin und Chirurgie des Rindes, 2006, pp. 1245-1254.
Dirksen., "Innere Medizin und Chirurgie des Rindes", Georg Thieme Verlag, 2006, pp. 1325 (English Abstract).
Ducusin et al., "Effects of extracellular Ca2+ on phagocytosis and intracellular Ca2+ concentrations in polymorphonuclear leukocytes of postpartum dairy cows", Research in Veterinary Science, vol. 75, Issue 1, Aug. 2003, pp. 27-32.
Enemark et al., "An evaluation of parameters for the detection of subclinical rumen acidosis in dairy herds", Veterinary Research Communications, vol. 28, Issue 8, 2004, pp. 687-709.
Evans et al., "Effects of Thymol on Ruminal Microorganisms", Current Microbiology, vol. 41, Issue 5, Nov. 2000, pp. 336-340.
Fürll et al., "Gebarpareseprophylaxe mit„Anionenrationen", Fortbildung—Rinder, 1996, pp. 4.
Gálfi et al., "Culture of epithelial cells from bovine ruminal mucosa", Veterinary Research Communications, vol. 4, Issue 1, 1980, pp. 295-300.
Garrett et al., "Diagnostic Methods for the Detection of Subacute Ruminal Acidosis in Dairy Cows", Journal of Dairy Science, vol. 82, Issue 6, Jun. 1999, pp. 1170-1178.
Gartner et al., "Untersuehungen iiber die Passage yon Harnstoff und Ammoniak durch die Pansenwand yon Ziegen", Pflüger's Archiv für die gesamte Physiologie des Menschen und der Tiere, vol. 274, Issue 3, Dec. 1, 1961, pp. 281-288.
Gasteiner et al., "Measuring rumen pH and temperature by an indwelling and wireless data transmitting unit and application under different feeding conditions", 2009, pp. 1-25 (English Abstract).
Gelfert et al., "Comparison of the impact of different anionic salts on the acid-base status and calcium metabolism in non-lactating, non-pregnant dairy cows", The Veterinary Journal, vol. 185, Issue 3, Sep. 2010, pp. 305-309.
Goff et al., "Effect of Mastectomy on Milk Fever, Energy, and Vitamins A, E, and β-Carotene Status at Parturition", Journal of Dairy Science, vol. 85, Issue 6, Jun. 2002, pp. 1427-1436.
Goff et al., "Oral Administration of Calcium Salts for Treatment of Hypocalcemia in Cattle", Journal of Dairy Science, vol. 76, Issue 1, Jan. 1993, pp. 101-108.

(56) References Cited

OTHER PUBLICATIONS

Goff et al., "Relative acidifying activity of anionic salts commonly used to prevent milk fever", Journal of Dairy Science, vol. 87, Issue 5, May 2004, pp. 1245-1255.
Harmeyer et al., "Aspects of Urea Metabolism in Ruminants with Reference to the Goat", Journal of Dairy Science, vol. 63, Issue 10, Oct. 1980, pp. 1707-1728.
Hartmann et al., "klinische pathologie der haustiere", 1994, pp. 622 (English Abstract).
Hoffmann., "Rinderkrankheiten Band 1 Innere und chirurgische Erkrankungen", 1992, pp. 444 (English Abstract).
Horn et al., "Dietary Buffers and Ruminal and Blood Parameters of Subclinical Lactic Acidosis in Steers", Journal of Animal Science, vol. 48, No. 3, Mar. 1979, pp. 683-691.
Horst et al., "Strategies for Preventing Milk Fever in Dairy Cattle", Journal of Dairy Science, vol. 80, Issue 7, Jul. 1997, pp. 1269-1280.
Horst et al., "Symposium: Calcium and Vitamin Calcium Metabolism and Utilization D Metabolism in the Dairy Cowl", Journal of Dairy Science, vol. 77, Issue 7, Jul. 1994, pp. 1936-1951.
Horst, R. L., "Regulation of Calcium and Phosphorus Homeostasis in the Dairy Cow", Journal of Dairy Science, vol. 69, Issue 2, Feb. 1986, pp. 604-616.
Jeroch et al., "Ernährung landwirtschaftlicher Nutztiere", 2008, pp. 544 (English Abstract).
Kennelly et al., "Influence of Carbohydrate Source and Buffer on Rumen Fermentation Characteristics, Milk Yield, and Milk Composition in Early-Lactation Holstein Cows", Journal of Dairy Science, vol. 82, No. 11, Nov. 1999, pp. 2486-2496.
Kimura et al., "Parturition and Hypocalcemia Blunts Calcium Signals in Immune Cells of Dairy Cattle", Journal of Dairy Science, vol. 89, Issue 7, Jul. 2006, pp. 2588-2595.
Kirchgeβner., "Tierernährung", Oct. 2011 (English Abstract).
Kleen et al., "Subacute ruminal acidosis (SARA): a review", Journal of veterinary medicine. A, Physiology, pathology, clinical medicine, vol. 50, Issue 8, Oct. 2003, pp. 406-414.
Kraft et al., "Klinische Labordiagnostik in der Tiermedizin", Schattauer Verlag, Nov. 25, 2013, pp. 955 (English Abstract).
Krause et al., "Understanding and preventing subacute ruminal acidosis in dairy herds: A review", Animal Feed Science and Technology, vol. 126, Issue 3-4, Mar. 9, 2006, pp. 215-236.
Lang et al., "Na transport in sheep rumen is modulated by voltage-dependent cation conductance in apical membrane", American Journal of Physiology, vol. 277, Issue 3, Sep. 1999, pp. G609-G618.
Leonhard-Marek et al., "Basolateral Mg2 /Na exchange regulates apical nonselective cation channel in sheep rumen epithelium via cytosolic Mg2", American Journal of Physiology—Gastrointestinal and Liver Physiology, vol. 288, Issue 4, 2005, pp. G630-G645.
Leonhard-Marek et al., "Transport of cations and anions across forestomach epithelia: conclusions from in vitro studies", Animal, vol. 4, Issue 7, Jul. 2010, pp. 1-20.
Littledike et al., "Sequential Sampling and Analysis of Renal Hydroxylase Activities of Cattle Given 1α-Hydroxyvitamin D3", Journal of Dairy Science, vol. 69, Issue 4, Apr. 1986, pp. 990-997.
Macheboeuf et al., "Dose-response effects of essential oils on in vitro fermentation activity of the rumen microbial population", Animal Feed Science and Technology, vol. 145, Issue 1-4, Aug. 2008, pp. 335-350.
Malz et al., "Neue Aspekte zur Pathogenese und Therapie der hypocalcämischen Gebärparese", Der praktische Ticrarzt, 1992, pp. 507-515.
Martens et al., "Magnesium transport by isolated rumen epithelium of sheep", Research in Veterinary Science, vol. 24, Issue 2, Mar. 1978, pp. 161-168.
Benchaar, C., et al., "Effects of monensin and increasing dose levels of a mixture of essential oil compounds on intake, digestion and growth performance of beef cattle", Can. J. Anim. Sci., vol. 86, Nov. 25, 2005, pp. 91-96.
Benchaar, C., et al., "A review of plant-derived essential oils in ruminant nutrition and production", Animal Feed Science and Technology, vol. 145, 2008, pp. 209-228.
Santos, M. B., et al., "Effects of addition of an essential oil complex to the diet of lactating dairy cows on whole tract ligestion of nutrients and productive performance", Animal Feed Science and Technology, vol. 157, 2010, pp. 64-71.
Dziba, L. E., et al., "Feeding Behavior of Lambs in Relation to Kinetics of 1,8-Cineole Dosed Intravenously or Into the Rumen", Journal of Chemical Ecology, vol. 32, No. 2, Feb. 2006, pp. 391-408.
Fandino, I., et al., "Anise and capsicum as alternatives to monensin to modify rumen fermentation in beef heifers fed a high concentrate diet", Animal Feed Science and Technology, vol. 145, Issues 1-4, Aug. 14, 2008, pp. 409-417.
Soltan, M. A., Effect of Essential Oils Supplementation on Growth Performance, Nutrient Digestibility, Health Condition of Holstein Male Calves During Pre- and Post-Weaning Periods, Pakistan Journal of Nutrition, vol. 8, Issue 5, 2009, pp. 642-652.
Soltan, M., et al., "Influence of Essential Oils Supplementation on Digestion, Rumen Fermentation, Rumen Microbial Populations and Productive Performance of Dairy Cows", Asian Journal of Animal Sciences, vol. 3, Issue 1, Jan. 2009, pp. 1-12.
Yang, W. Z., et al., "Dose response to cinnamaldehyde supplementation in growing beef heifers: ruminal and intestinal digestion", Journal of Animal Science, vol. 88, Issue 2, 2010, pp. 680-688.
Zhang, T.-T., et al., "Effects of dose and adaptation time of ginger root (*Zingiber officinale*) on rumen fermentation", Journal of Animal and Feed Sciences, vol. 20, Issue 3, Jan. 2011, pp. 461-471.

\* cited by examiner

COMPOSITIONS FOR ALLEVIATING GASTROINTESTINAL TRACT DISORDERS OR ASSOCIATED SYSTEMIC DISORDERS IN RUMINANTS AND CAMELIDS

CROSS-REFERENCE TO A RELATED APPLICATION

This application is a national phase patent application of International patent application PCT/EP 2013/066094, filed on Jul. 31, 2013, which claims priority of German patent application 10 2012 015 029.6, filed on Jul. 31, 2012.

TECHNICAL FIELD

The present invention relates in an aspect to feed supplements for alleviating gastrointestinal tract disorders and associated systemic disorders in an animal from the suborder of the ruminants (Ruminantia) or the (ruminant) tylopods (Tylopoda), methods for producing such feed supplements as well as feeds and feed additives containing such feed supplements. Furthermore, the present invention relates in an aspect to medicaments for the treatment of diseases which are associated with disorders of the gastrointestinal tract, particularly rumen acidosis and/or parturient paresis.

BACKGROUND

In present-day livestock management gastrointestinal metabolism disorders occur frequently, because their feeding had to be changed on account of the requirements of modern animal husbandry to ensure sufficient maintenance as well as growth of the animal mass for meat production and, moreover, sufficient production of products such as milk. It proves to be problematic here, among other things, that the resorption capacity of the gastrointestinal organs does not keep up with the demand.

The standard ration of a ruminant is green fodder in the form of grasses and cellulolytic byproducts from agricultural production. These are either fed fresh as pasture grass or cutting grass, in a dry form as hay or in a preserved state as silage. The ability to use these materials as food sources is only possible on account of a pre-gastric bacterial fermentation in the rumen, the section of the animal stomach that is not fundus-like. Here, a bacterial effect reduces the carbohydrates with a complex structure, cellulose, hemicellulose and lignin and the associated non-structure carbohydrates, pectin, starches and sugars to short-chain fatty acids, which are resorbed via the rumen wall and enter into the carbohydrate metabolism. Apart from the fatty acids nitrogen derivatives such as ammonia and electrolytes such as sodium, calcium and magnesium are also resorbed via the rumen wall and absorbed into the blood.

The microorganisms growing in the rumen are subjected to digestive action in the fundus-like stomach and small intestine after the efflux from the rumen and constitute the essential source of protein of the ruminant, whereas proteins contained in the feed are degraded by the microbial flora of the rumen predominantly to ammonia, which has to re-enter into the microbial protein biosynthesis in order to be utilized by the animal.

The adaptation of ruminants to a pre-gastric digestion has developed a system of retaining the ration that was taken in, which constitutes a significant part of the mechanism for the maximum extraction of energy from hard-to-digest structural carbohydrates. This retention requires a certain abstinence when taking in food, which is further restricted in foods that are based on green fodder, since the coarser ingested food needs to be retained longer in order to achieve an effective extraction of energy. This constitutes a special problem in modern domesticated ruminants, as the demand for nutrients created by a genetic selection with regard to a more rapid lean muscle growth or high levels of milk production to a great extent exceeds the supply formed by a fermentation of the ration based on green fodder.

The ration that has to be fed requires the addition of large amounts of non-structure carbohydrates (starches and sugars), which are fed in the form of grains. Furthermore, a supplementary feeding of nutrients rich in protein (e.g. soybean meal or legumes) is necessary to meet the demand for proteins. These additives lead to an accelerated fermentation activity in the rumen, wherein high concentrations of short-chain fatty acids and ammonia are released, which often constitute a source of physiological and metabolic stress. In particular, this often leads to an acidotic crisis of the rumen environment (rumen acidosis). As a consequence, feeding strategies must try to maximize the use of green fodder without negatively affecting the delivery of nutrients necessary for maintenance and production. Alternatively, one can try to optimize the resorption of the fermentation products produced in the rumen fermentation so that less or no gastrointestinal disorders, such as e.g. the rumen acidosis, occur.

Recommended treatments for rumen acidosis, as one of the most common gastrointestinal disorders or illnesses include the administration of a mixture of sodium bicarbonate, formaldehyde, magnesium oxide and carbon in order to kill the rapidly dividing bacteria (NebGuide G91-1047-A). However, the degradation of structural fibers from green fodder, hay or silage by bacterial enzymes, which is necessary for the further passage, is hereby also inhibited. To neutralize the acids produced during fermentation buffers are widely used (Horn, 1979, Kennelly, 1999), but do not appear to be effective enough to satisfy the animal industry. The palatability of most buffers is low and requires careful handling in order to avoid reduced feed intake. Ionophore antibiotics such as monensin, lasalocid and salinomycin are generally effective against gram-positive bacteria, including the main ruminal lactate-forming bacteria, *S. bovis* and species of *lactobacillus* (Burrin and Britton, 1986, Coe, 1999, Nagaraja, 1985). Hence, they are effective in preventing acute acidosis during the transition to high-concentrate feeding when cattle first arrive at the feedlots or after calving and stabilize the rumen pH. However, ionophores also reduce the feed intake. It has also been shown that other classes of antibiotics prevent or improve acute acidosis, including virginiamycin in sheep (Thorniley et al., 1998) and the sulfur-containing peptide antibiotic thiopeptin, which is especially effective against *S. bovis* (Armstrong, 1984). However, the continuous use of antibiotic feed additives is no longer viewed as a suitable management instrument due to, among other things, the development of resistance with consequent effects for humans (for an overview see: The use of drugs in food animals: benefits and risks, 1999).

In a further frequently occurring gastrointestinal disorder or disease, parturient paresis, the blood calcium level drops to values that lead to malfunctions in the neuromuscular stimulus conduction followed by paralysis. Causes are the high losses of calcium with the milk, the insufficient resorption capacity of the gastrointestinal tract and the insufficient mobilization from the body's reserves (bones and plasma proteins). The alkalotic metabolism status of the ruminant contributes to this. As therapy, usually differentiated feed is administered prior to and after calving, wherein mineral feed without calcium is administered in the dry period and mineral feed rich in calcium is administered beginning with the birth. Alternatively, high doses of calcium salts and vitamin D are administered. However, high doses of vitamin D can lead to irreversible calcifications of the soft tissue (Littledike et al., 1986) and the differential feeding is costly to carry out. Furthermore, vitamin D encourages the integration of calcium in the bone, which may result in a further drop in the blood calcium levels. When high concentrations of calcium salts are administered, this indeed leads to a partial correction of the alkalotic metabolism status of the animal with the ensuing ability to increasingly mobilize calcium from the bone (Goff and Horst, 1993), however, this is often accompanied by a decreased calcium absorption if the supplementary feeding lasts too long. Calcium doses that are too high can herein even be toxic (Goff et al., 2002). Furthermore, so-called "anionic" or "acidic" salts such as e.g. ammonium sulfate are employed (Goff et al. 2004; Gelfert et al. 2010), with which the alkalotic metabolism status of the ruminant is to be corrected in order to encourage the mobilization of calcium from bones and plasma proteins. However, a reduction of feed intake must also be reckoned with here. The parturient paresis still constitutes a considerable yield-reducing complication, and there is a demand for new feed supplements or means to prevent and alleviate the disease here also.

Based on this background, it was the object of the present invention to provide feed supplements which as feed supplement or as an integral component of a feed are suited to guarantee an optimal utilization of feeds in animals from the suborder of the ruminants (Ruminantia) or the (ruminant) tylopods (Tylopoda) by obviating the development of metabolically induced subclinical disorders or manifest diseases, such as e.g. rumen acidosis or parturient paresis, increase the protein utilization and/or improve the ingestion/performance ratio of the animal (e.g. milk production).

SUMMARY

To achieve the object, the present invention provides in an aspect feed supplements containing substances which can modulate the activity of one or various Transient Receptor Potential (TRP) channels and thus be classified as agonists and/or antagonists of these channels. For this, feeding methods according to an aspect of the invention are proposed, which comprise the supplementary feeding or pharmacological administration of one or multiple of the TRP agonists and/or antagonists noted in the appendix, or of feed supplements containing one or multiple of these TRP modulators in a concentration range of 0.01 to 10 g/kg feed for influencing the resorption processes in ruminants as well as in camelids.

Without wishing to be bound by theory, it is assumed on account of the results shown in the examples that TRP modulators can modulate the speed with which cations such as ammonium, calcium, magnesium and protons are resorbed from the rumen. As a further effect, the TRP modulators or feed supplements containing them according to an aspect of the invention influence the resorption of the mentioned ions from the rumen in such a way that the effect is an improvement of disorders of the gastrointestinal tract. Furthermore, due to the change in the resorption event in the gastrointestinal tract an improvement of the state of health and/or of the performance of the animal takes place, wherein e.g. an increased integration of ammonia into microbial protein utilizable for the animal takes place with a reduced release into the environment. In an embodiment, the feed supplements according to an aspect of the invention in this case do not influence the microflora in the intestines of the ruminants or tylopods.

Alternatively or additionally, TRP modulators and the compositions containing them are provided for use in the alleviation of an illness in the gastrointestinal tract of an animal.

With a normalization of the pH value in the rumen lumen, furthermore, an improved bacteria growth with an increased use of the remaining ammonia for the protein biosynthesis is expected.

Figure 1:
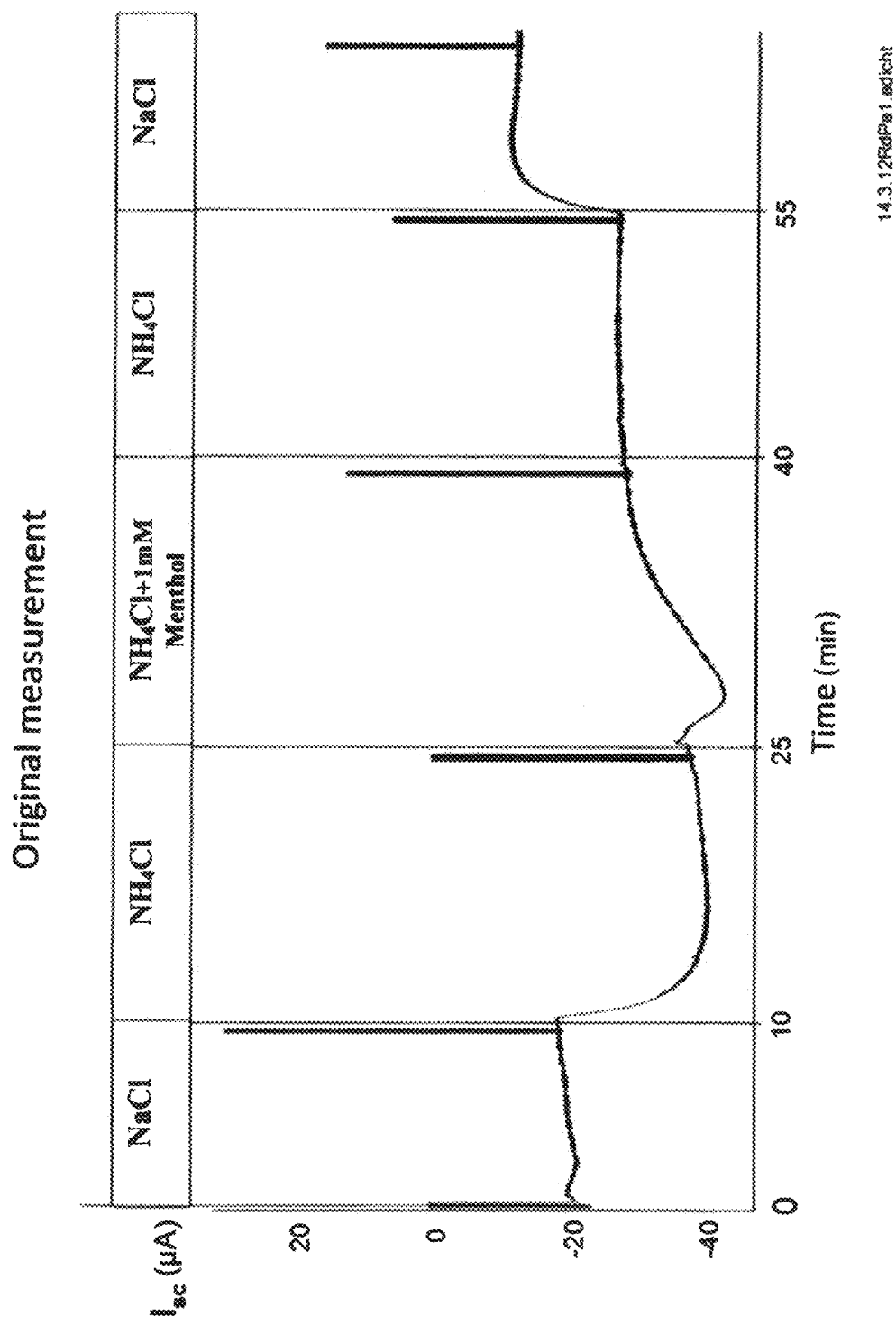
FIG. 1: Measurement of the transepithelial current across rumen epithelium from cattle. The addition of 40 mM $NH_4Cl$ to the mucosal solution (Ringer) leads to a considerable rise in the short-circuit current ($I_{sc}$). The additional adding of menthol (1 mM) as TRP modulator leads to a further rise in that current, wherein it is assumed that ion channels permeable for $NH_4^+$ ions open up.
Figure 2:
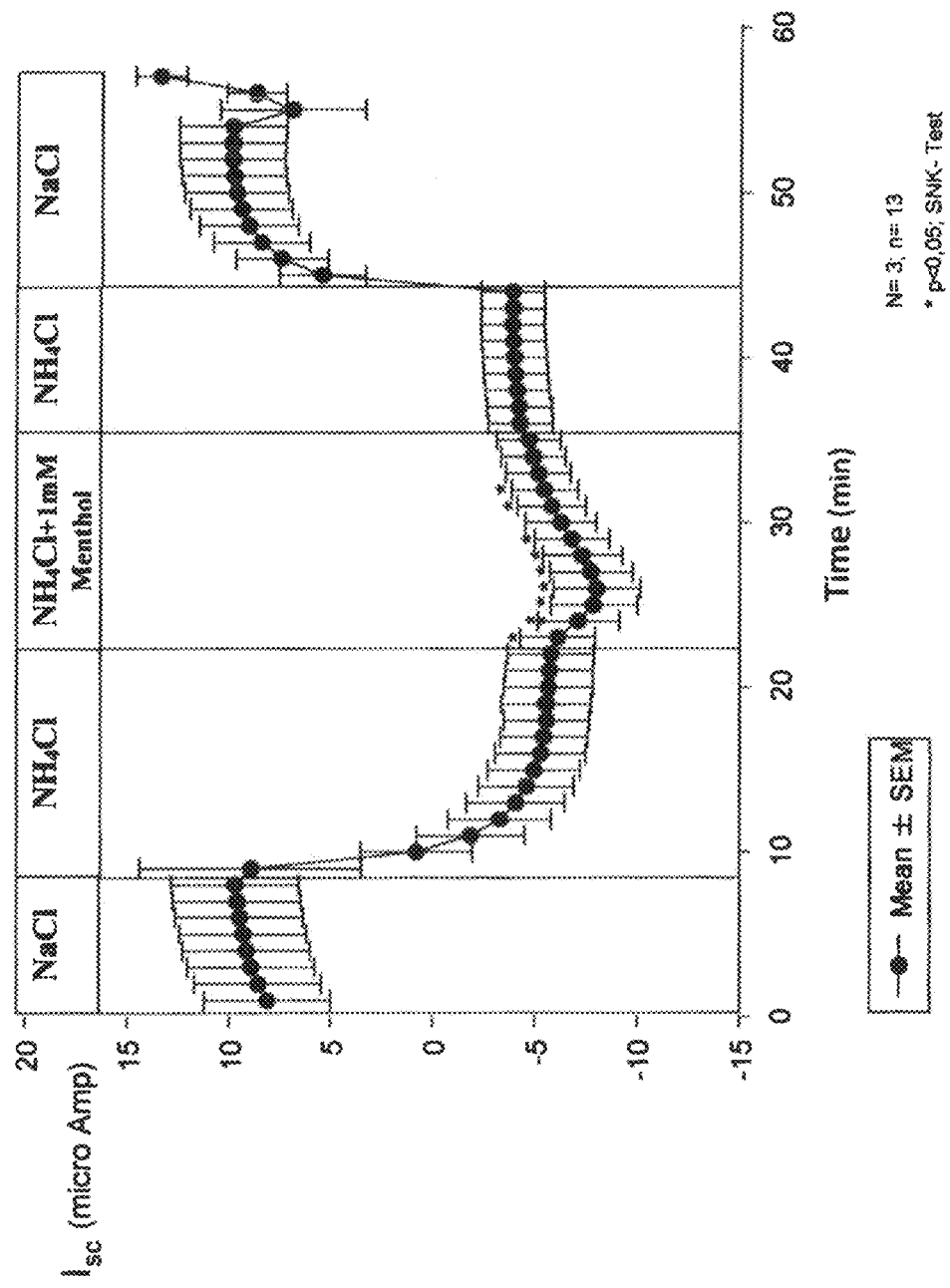
FIG. 2: Summary of the results. The mean values of the transepithelial current ($\pm$SEM) over time from 13 individual measurements on three different epithelia were plotted as in FIG. 1. After adding menthol (1 mmol·l$^{-1}$) as TRP modulator there is a statistically significant increase in the current across the epithelium ($p<0.05$, Student-Newman-Keuls). Similar results were also observed in experiments in which a lower dose (200 µmol·l$^{-1}$ menthol) was given.
Figure 3:
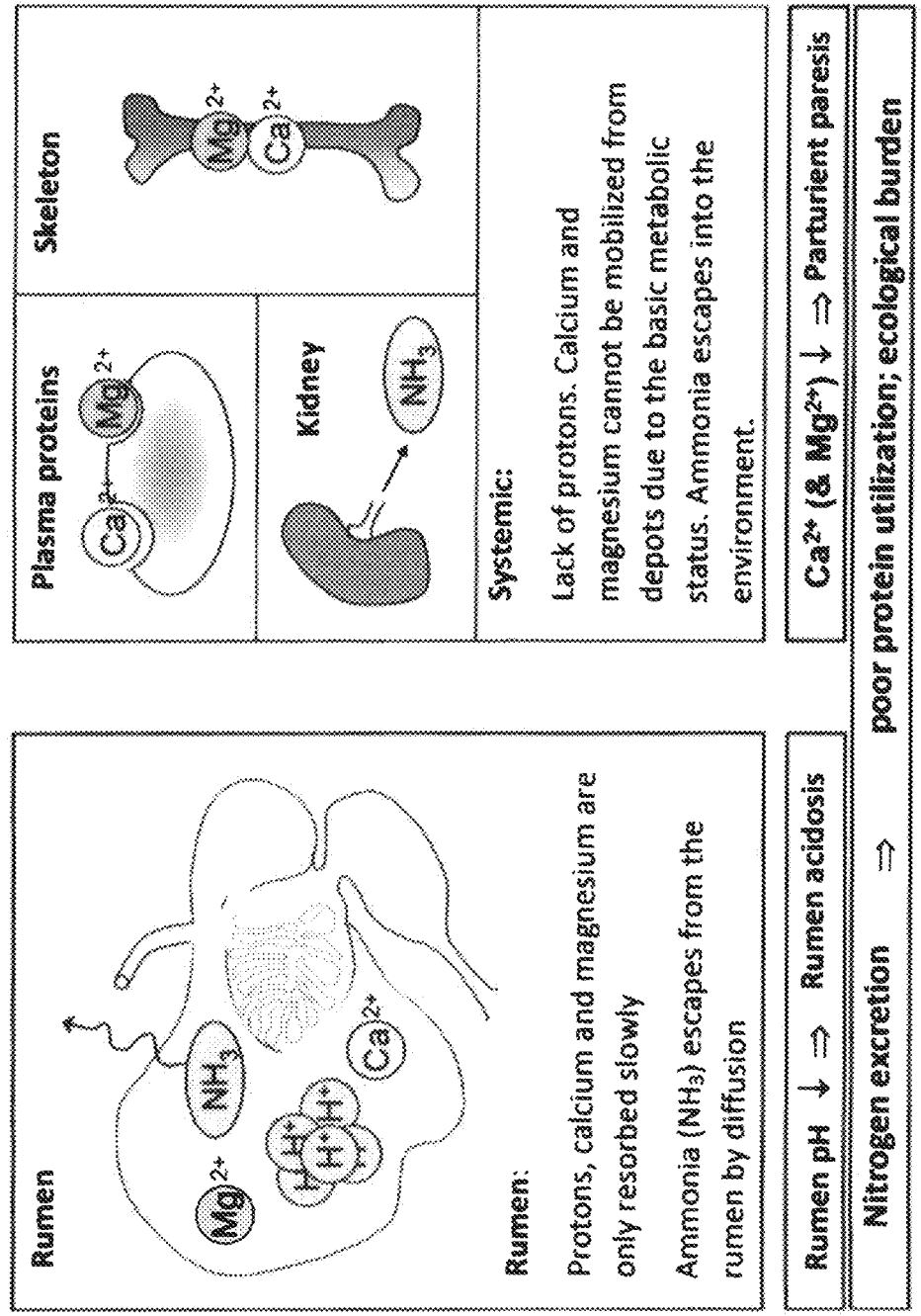
FIG. 3: Problems of the ruminant. The resorption capacity of the rumen for cations such as calcium, magnesium and $H^+$-ions (protons) is limited. This leads to an acidotic crisis in the rumen with a reduction of the protein utilization. A systemic proton deficiency (=basic metabolism status or alkalosis), however, is found, which makes the mobilization of calcium and magnesium from the depots in bones and plasma proteins more difficult. Ammonia ($NH_3$) escaping from the rumen exacerbates the rumen acidosis and the systemic alkalosis. In addition, the conversion of ammonia into microbial protein for milk and meat production is prevented. The systemically absorbed ammonia is toxic, must be excreted and leads to environmental pollution.
Figure 4:
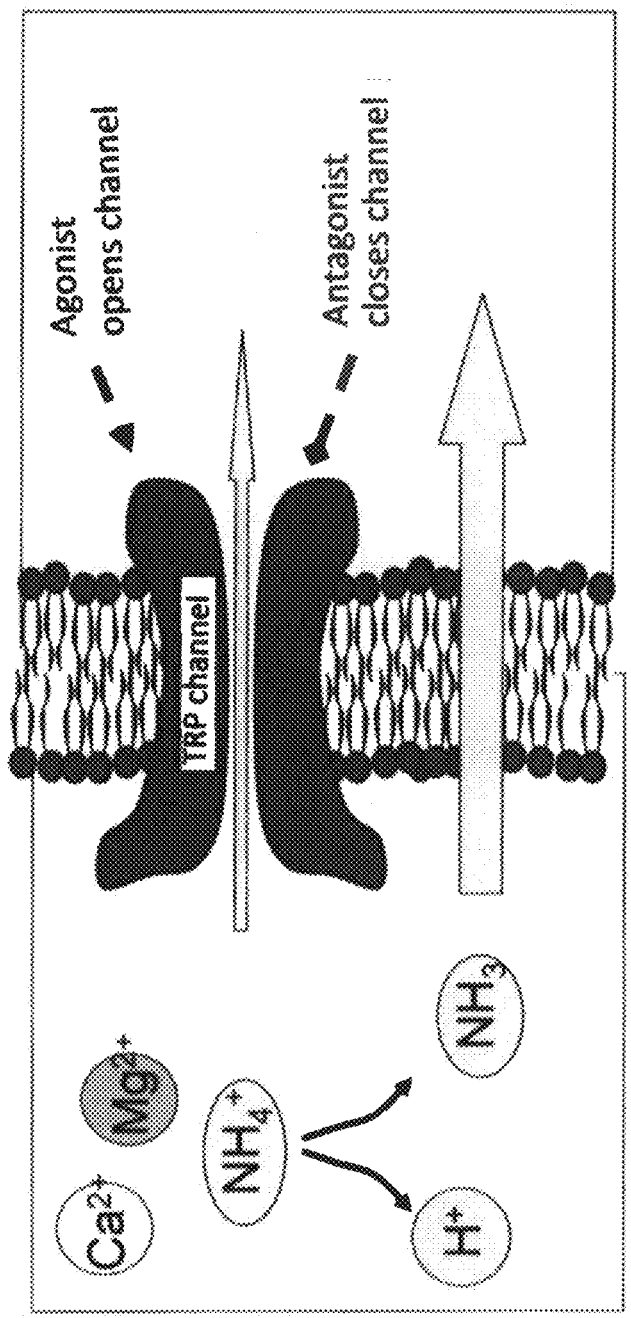
FIG. 4: Resorption of ammonia/ammonium from the rumen. The ammonium ($NH_4^+$) present in the rumen continuously breaks down into ammonia ($NH_3$), wherein a proton ($H^+$) is split off. The $NH_3$ rapidly escapes from the rumen, since the lipid membrane of the rumen epithelium cells is highly permeable for lipid-soluble substances such as ammonia ($NH_3$). The proton stays behind and acidifies the rumen, while the invasion of ammonia ($NH_3$) into the cell and thereafter into the organism contributes to the development of an alkalosis (=basic metabolism crisis). Alternatively, ammonium ($NH_4^+$) can get across the cell membrane. Nonselective cation channels act as a transport path, directing numerous cations across the rumen epithelium, among them also calcium and magnesium (Martens and Harmeyer 1978; Lang and Martens 1999; Schweigel, Lang et al. 1999; Abdoun, Stumpff et al. 2005; Leonhard-Marek, Stumpff et al. 2005). Numerous agonists and antagonists regulate the permeability of these channels for cations via various mechanisms and thus, when exposed, cause the triggering of sensory perceptions (Ramsey, Delling et al. 2006; Xu, Delling et al. 2006; Vriens, Nilius et al. 2008).
Figure 5:
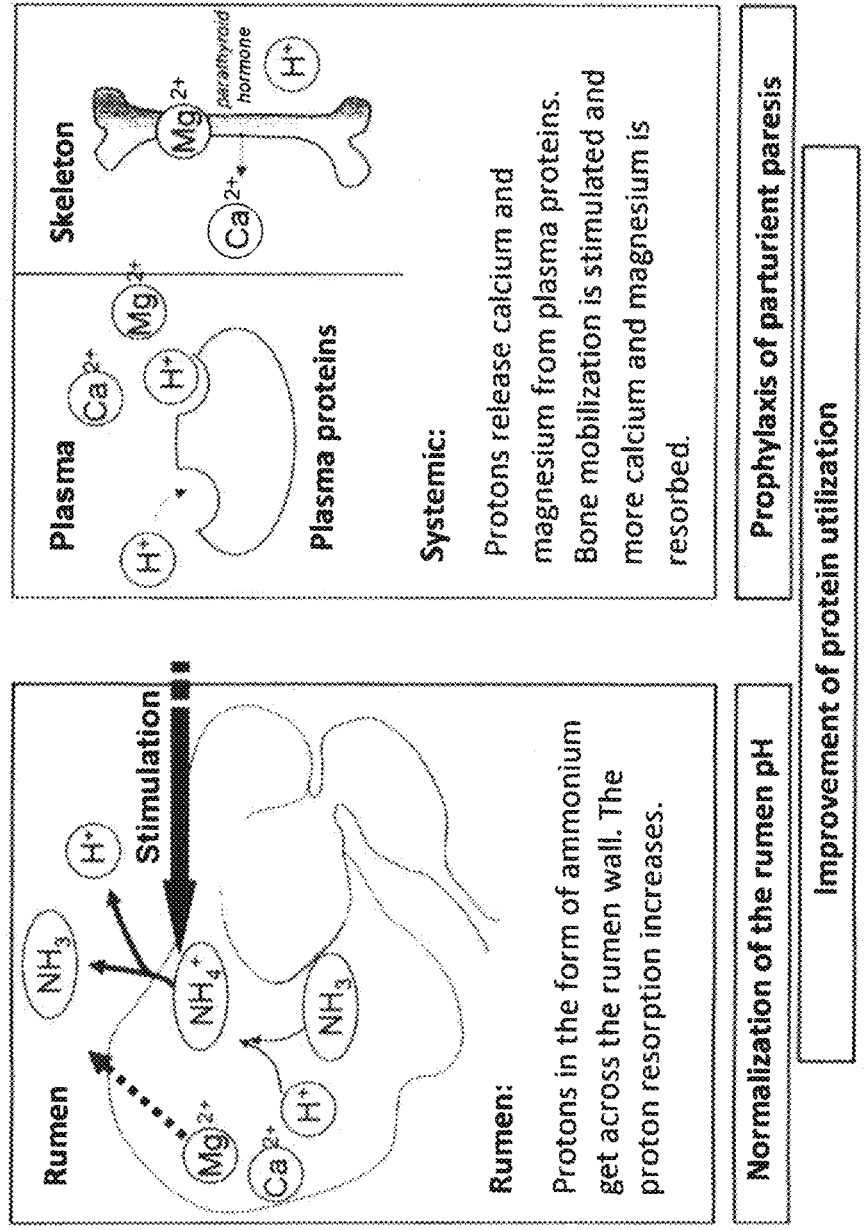
FIG. 5: Increasing the cation conductivity: By giving a TRP agonist the resorption capacity of the rumen for cations is enhanced. Nitrogen, which cannot be utilized by the bacteria, gets across the rumen wall mainly in the protonated form as ammonium ($NH_4^+$). Hereby, protons are removed from the rumen lumen and the rumen pH normalizes. At the same time, the systemic alkalosis is corrected. Protons oust calcium and magnesium from the bond with plasma proteins and stimulate the secretion of parathyroid hormone for the mobilization from the bone. An improved resorption capacity of the rumen epithelium for cations—among them calcium, magnesium, and protons—supports the effect. The level of calcium and magnesium in the plasma normalizes and prevents the occurrence of conditions of calcium deficiency such as the parturient paresis.
Figure 6:
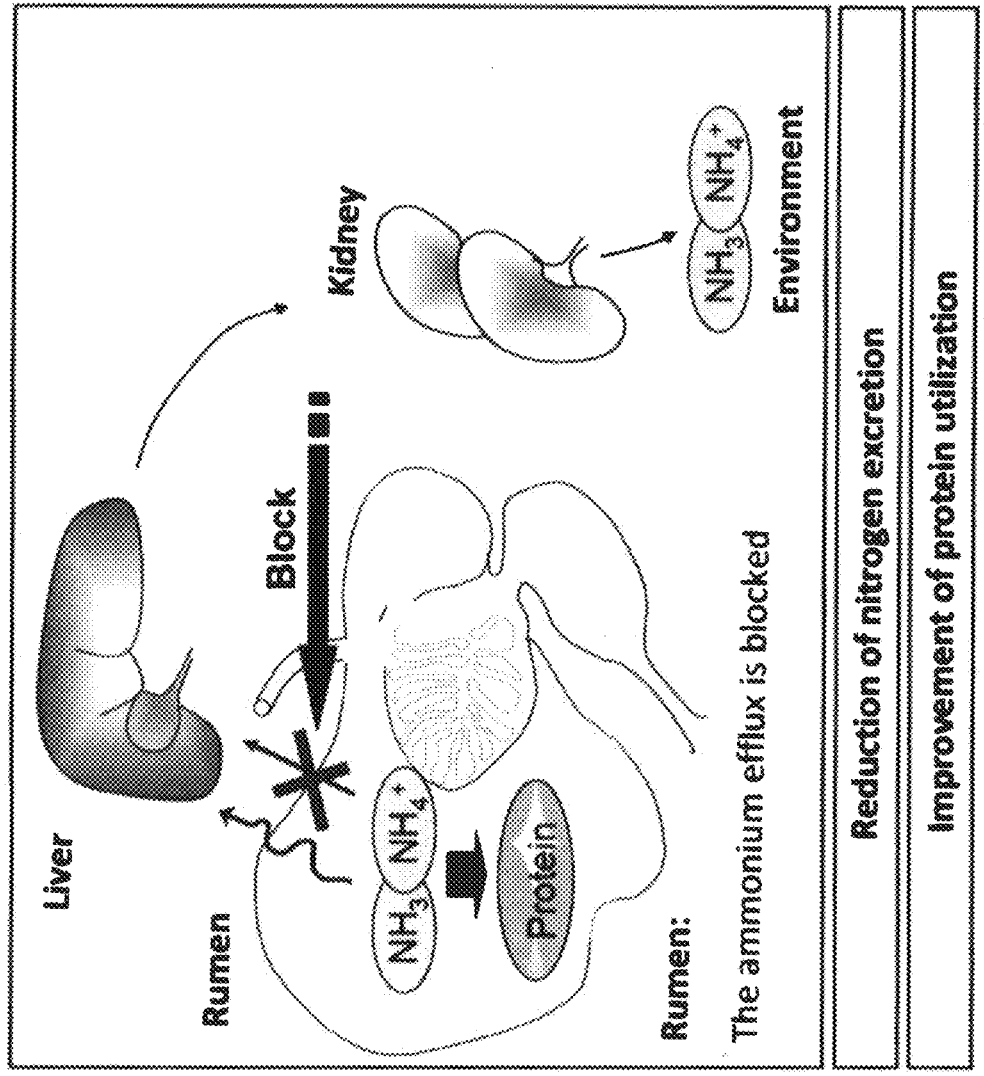

FIG. 6: Decreasing the ammonium conductivity: By giving a TRP antagonist the resorption of ammonium ($NH_4^+$) across the rumen wall is reduced. More nitrogen stays in the rumen and can be integrated into bacterial protein. The supplementary feeding of proteins can be reduced, the strain on the liver eases and less nitrogen gets into the environment. As a simultaneous reduction of the calcium and proton absorption cannot be ruled out, this form of application should be taken into consideration first of all with beef cattle, among which parturient paresis (=hypocalcemia) does not occur. It also seems conceivable, however, that among the substances to be protected there are those which modulate the permeability of the pore in such a way that more and more divalent cations such as calcium and magnesium are absorbed while the univalent cations (such as ammonium) are ousted from the pore. A rise in the occurrences of rumen acidosis is expected as a possible undesired side effect of giving a TRP antagonist. TRP antagonists can e.g. be employed in free-range animal husbandry with a high share of crude fiber feeds. Here, the rumen acidosis occurs less frequently.

Figure 7:
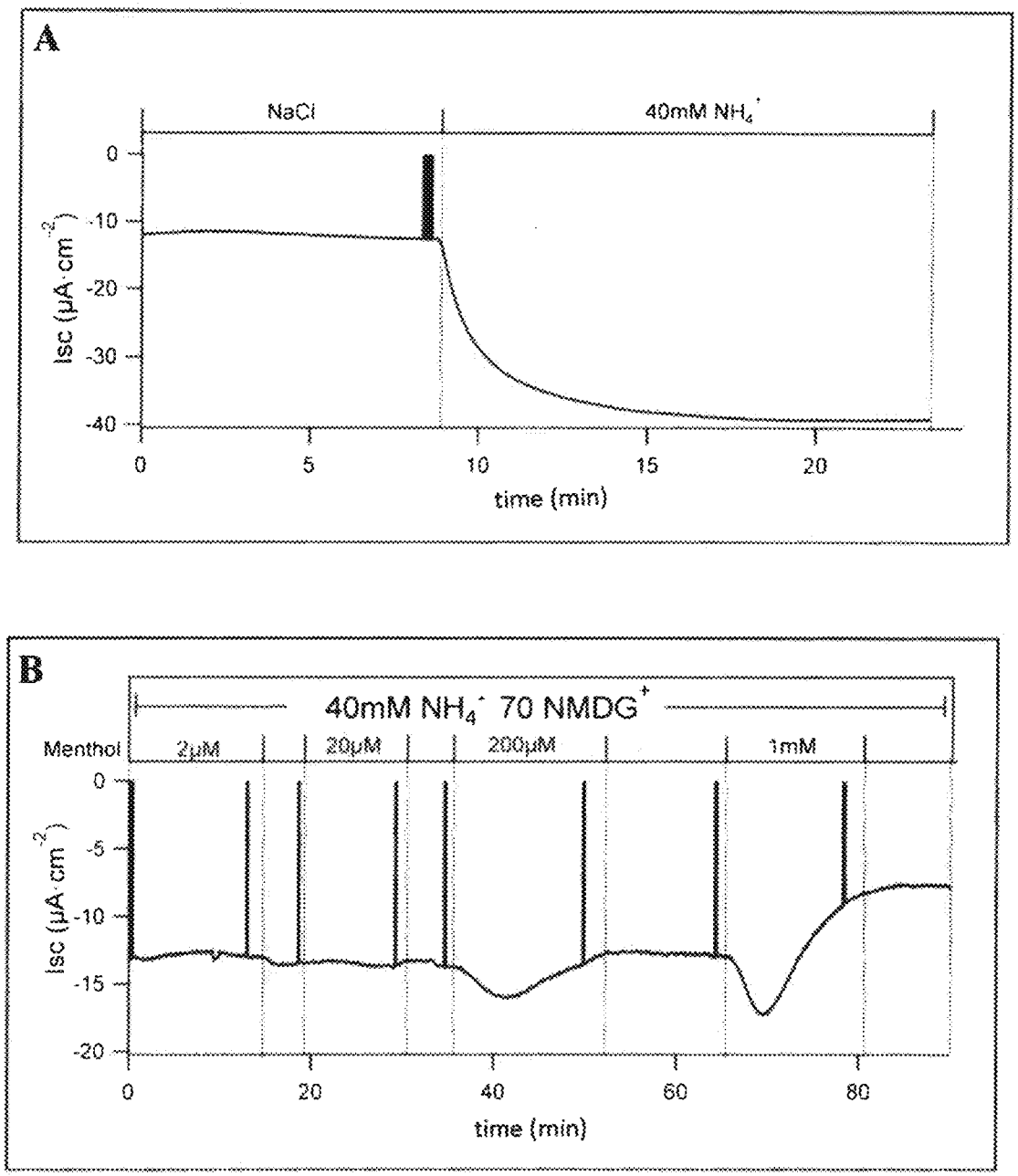

FIG. 7: Measurements in the horizontal Ussing chamber. A: Replacing 40 mM NMDG+ with an equimolar amount of $NH_4^+$ leads to a significant rise in the transepithelial current. The measurement proves that the epithelium transports ammonium in the ionized form. B: Effects of rising concentrations of menthol on the transepithelial current.

Figure 8:
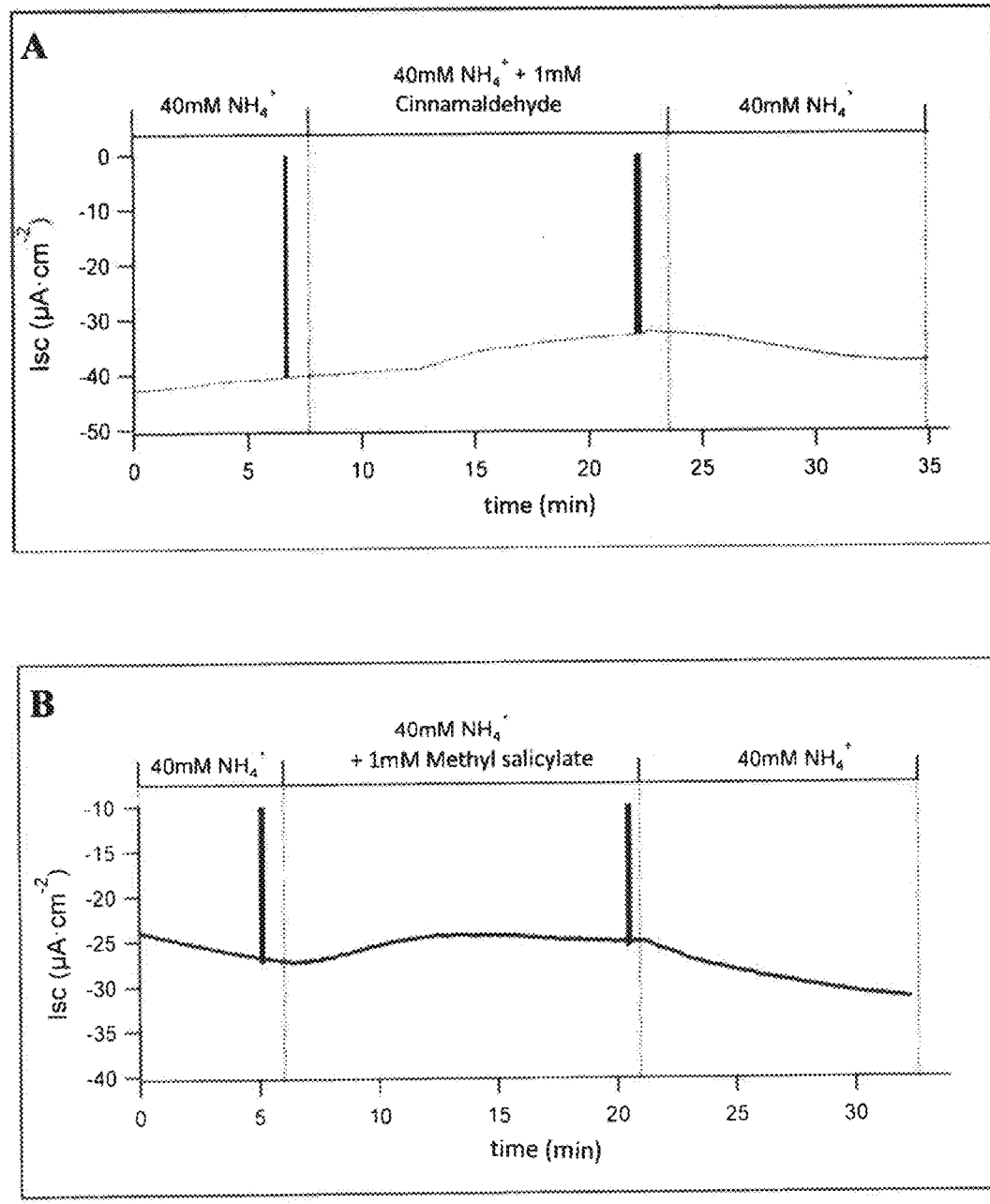

FIG. 8: Measurements in the horizontal Ussing chamber. A: Effect of cinnamaldehyde on the transepithelial current. B: Effect of methyl salicylate on the transepithelial current.

Figure 9:
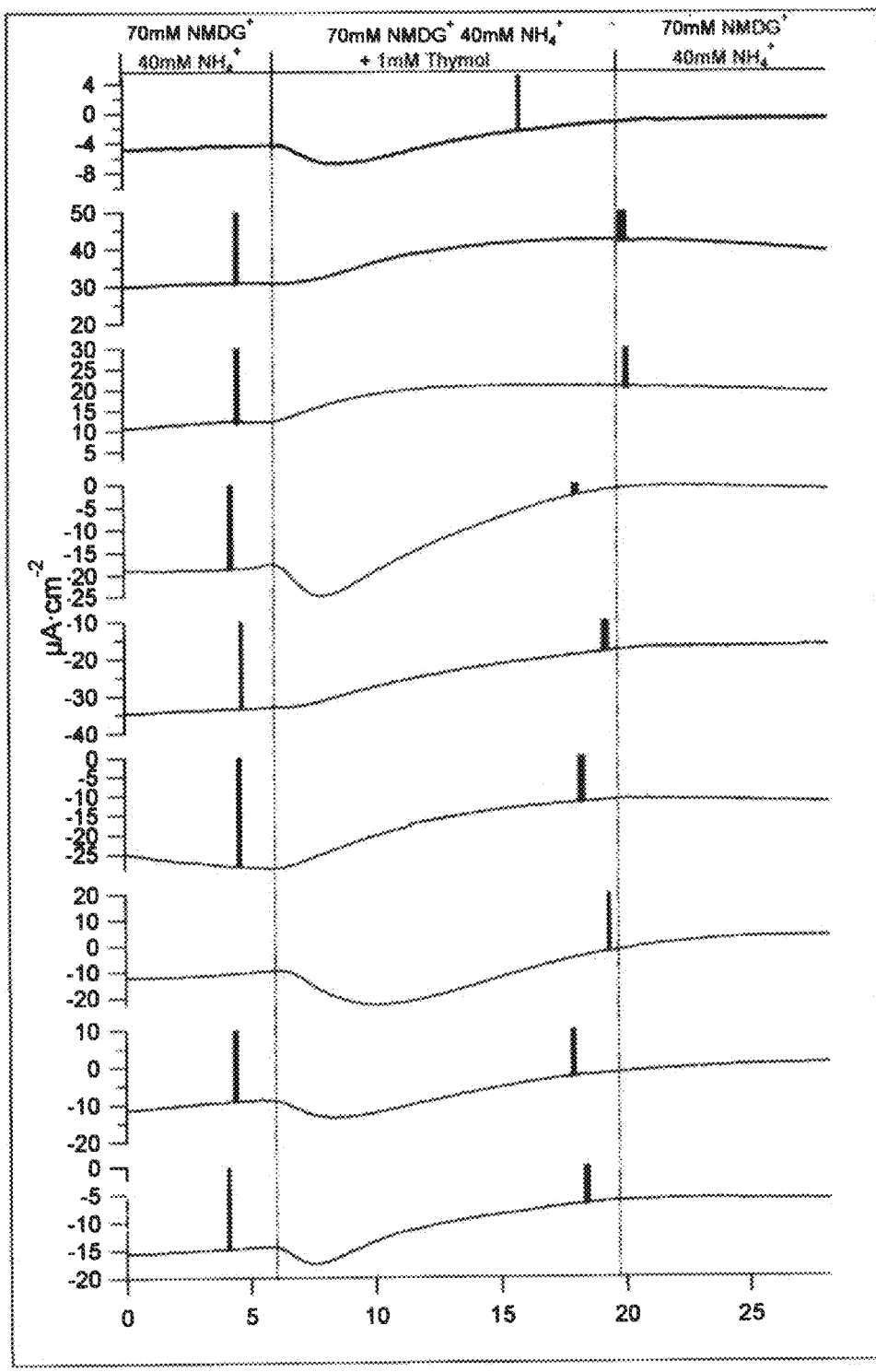

FIG. 9: Measurements in the horizontal Ussing chamber. Comparative view of nine measurements in which 1 mM thymol was given into a perfusion solution containing NH4+ without Na+.

Figure 10:
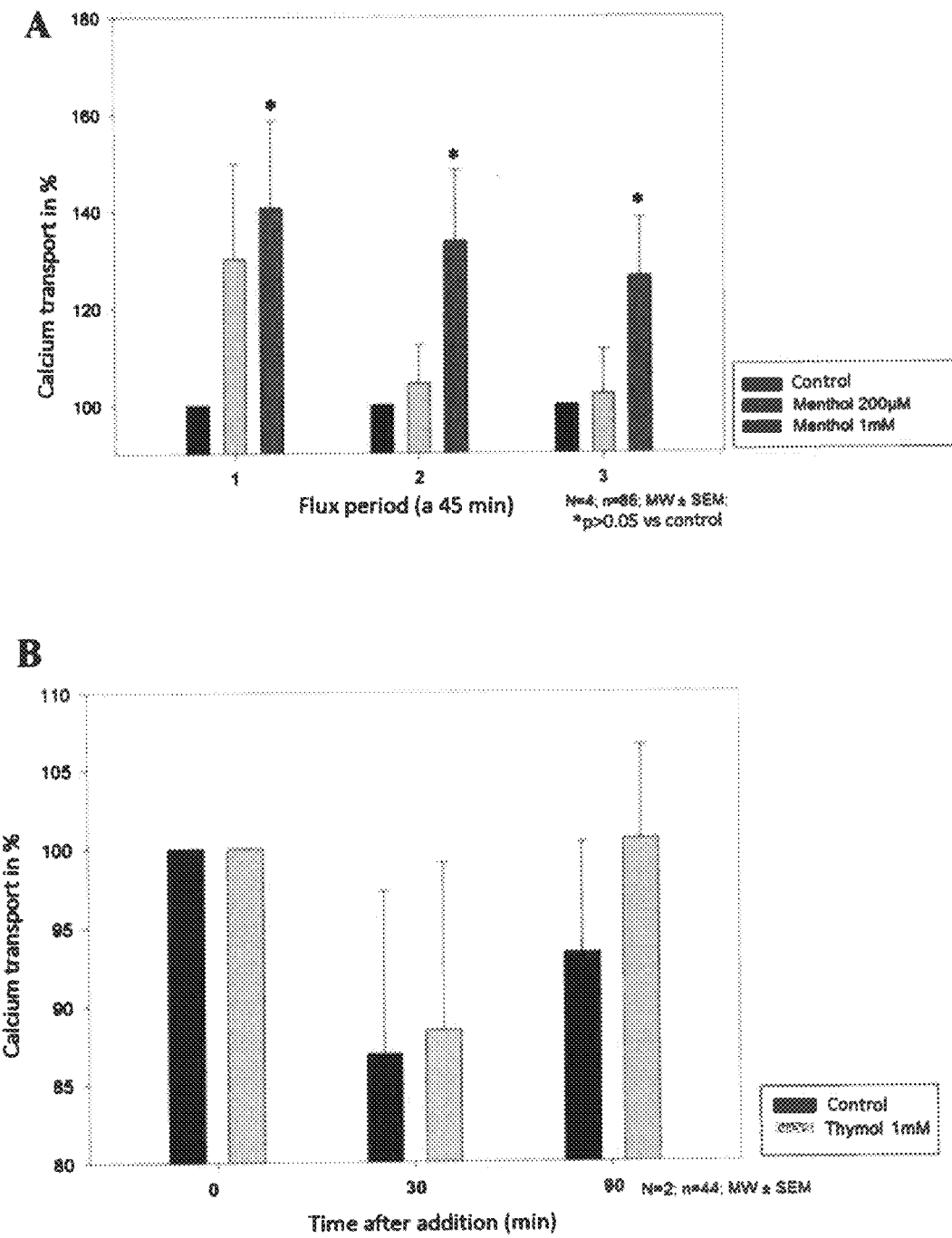

FIG. 10: Calcium flux across the rumen epithelium. A: Concentration-dependent increase in the calcium transport across the rumen tissue after adding menthol in two different concentrations compared to the control group. N=4 (cattle) n=85 (epithelia). B: Change in the calcium transport across the rumen tissue after adding thymol compared to the control group. N=2 (one cow, one sheep); n=44 (epithelia).

DEFINITIONS AND TERMS

Unless subsequently the context clearly indicates otherwise, the use of singular forms or plural forms always comprises both the plural and the singular.

The term "composition" as defined by the invention comprises medicaments and feed additives and is characterized in that at least one of the components or ingredients is a TRP channel modulator as defined by the present invention. Examples of TRP modulators as defined by the present invention are listed in tables 10 to 13. A "TRP modulator" is understood to be a substance that activates one or multiple TRP channels ("TRP agonist") or inhibits one or multiple TRP channels ("TRP antagonist") or also substances that have different effects on different TRP channels.

TRP channel proteins form TRP channels comprising six transmembrane domains which mediate the cation flow corresponding to their electrochemical gradients, whereby the intracellular Ca2+ and Na+ ion concentrations are raised and the respective cell is depolarized. Other cations can also pass the pore, wherein the selective permeability depends on the channel type (Owsianik, Talavera et al. 2006). According to the prevalent nomenclature, the genes for the 28 known channel subunits are divided into 7 families.

Many of the TRP channels can be activated by multiple stimuli. This polymodal sensitivity suggests that the physiologically relevant stimuli of a specific TRP channel depend on the respective cellular context. Furthermore, the cooperation between different TRP channels entails that with respect to interacting substances it is not always easy to make the distinction between an agonist and a modulator.

The TRP channels have manifold functions as sensors, which enable individual cells and the respective organism to detect changes in the surroundings, comprising temperature changes, detection of touch, pain, taste, and of specific chemical substances (see Ramsey et al., 2006; and Vriens et al., 2008). But there is also evidence of a participation of these channels in the epithelial resorption of calcium (Lambers, Bindels et al. 2006) and magnesium (Voets, Nilius et al. 2004).

Based on the results of the experiments shown here, when adding the TRP agonists and/or antagonists a change (increase when employing agonists; inhibition when employing antagonists) of the electrophysiological parameters and the transport rates across the rumen epithelium is to be expected.

The "TRP channel family" relevant to the mammal consists of six subfamilies:
TRPC (classic)
TRPV (vanilloid receptor)
TRPM (melastatin)
TRPA1 (ANKTM1)
TRPP (polycystin)
TRPML (mucolipin)

These subfamilies can be divided into subgroups, numerous ones of which are expressed in the gastrointestinal tract of the mammal.

As defined by the present invention, particularly the respective agonists and/or antagonists of the following channels: TRPV1, TRPV2, TRPV3, TRPV4, TRPV5, TRPV6
TRPA1, TRPM3, TRPM5, TRPM6, TRPM7, TRPM8
are understood to be TRP agonists and/or antagonists.

It arises from the terms and the function of the TRP channels as ion channels that an agonist essentially increases the ion conductivity of the rumen epithelium across the respective influenced channel, whereas an antagonist reduces it.

The term "ruminants" or "Ruminantia" as defined by the invention comprises animals from the suborder of the even-toed ungulates (Artiodactyla), which are characterized by a multi-part ruminant stomach, allowing the animals, among other things, an efficient digestion of cellulose. In these animals, the stomach divides into four compartments, the three forestomachs, namely the rumen (also paunch), the reticulum (also bonnet), the omasum (also manyplies or psalterium) and the main stomach, the abomasum (also Abomasus). Allocated to the ruminants are, consequently, animals from the families of the giraffids (Giraffidae), the musk deer (Moschidae), the antilocaprids (Antilocapridae), the deer (Cervidae) and the bovids (Bovidae). In particular, as defined by the present invention, animals from the group comprising: cattle, sheep, goats, giraffes, yaks, red deer, fallow deer, moose, roe deer, antelopes, buffalo and bison are counted among the ruminants.

The term "(ruminant) tylopods (Tylopoda)" as defined by the invention comprises animals from the suborder of the even-toed ungulates, whose stomach structure resembles the one in ruminants despite a lack of homology. Compared to the ruminants, it has a reduced omasum, which for this reason is partially depicted as tripartite. Allocated to the tylopods are animals from the family of camelids (Camelidae), the genera of camels (*Camelus*), llamas (*Lama*) and vicuñas (*Vicugna*). In particular, as defined by the present invention, animals from the group comprising: Bactrian camels, dromedaries, alpacas, llamas, guanacos and vicuñas are counted among the tylopods.

The term "rumen acidosis" comprises a metabolism disorder in ruminants and in tylopods, which mainly occurs as a result of too large amounts of feeds rich in carbohydrates and too small amounts of feeds rich in structure in the ration (Dirksen et al., 2002). Rumen acidosis is characterized by a strong acidity of the rumen, i.e. a low pH value of the ruminal fluid, usually below pH 5.5 (the standard value is at approximately pH 5.9 and above). Rumen acidosis can lead to considerable disturbances in the composition of the rumen flora and consequently to an injury of the rumen mucosa (chemical burn).

The pH of the ruminal fluid can be measured after sampling it. Retrieving a sample can take place by means of an orally inserted probe, but the informative value herein is affected by the strongly alkaline saliva. For this reason, the ventrolateral extraction by puncture of the caudoventral rumen sac (rumeno-centesis), as specified in Nordlund et al. 1994 and 1995, is better suited for the sampling of ruminal fluid. Alternatively, the pH value can also be recorded over a longer period of time directly in the stomach by employing a probe/bolus (e.g. by the company smaXtec animal care sales GmbH; Graz, AUSTRIA), and be read wirelessly, as specified e.g. in Gasteiner et al., (2009) in the section material and method on pages 3-5, the disclosure of which is hereby incorporated by reference into the present application. The measurement should always take place with multiple animals of a herd approximately 2 to 4 hours after feeding, wherein the diagnosis of a rumen acidosis is considered to be confirmed if a low pH is detected in at least 25% of the animals.

Acute rumen acidosis is characterized by a steep decline in the pH value with a high concentration of ruminal lactic acid (50-100 mM). The ruminal microbial population undergoes a significant shift, wherein the number of gram-positive bacteria forming lactic acid increases greatly. The dropping pH leads to the death of gram-negative bacteria and to a reduction or the complete disappearance of flagellated protozoa. The subacute rumen acidosis (pH between 5.2 and 5.8) and the chronic-latent metabolic acidosis are characterized by a reduced feed intake (loss of appetite) and thus a lower physical performance, including milk and beef performance (Enemark et al., 2004, Garret et al. 1999). It can also lead to changes in the consistency of the feces, which can have a grey-green color and be pasty to soupy. In a moderately severe manifestation of the rumen acidosis, the ruminant stops taking in food and the milk flow runs dry. Further symptoms are severe digestive disorders such as colic and diarrhea as well as apathy, unsteadiness and lameness. In accordance with the presence of symptoms or the lack/weak manifestation thereof, the rumen acidosis can be classified as subclinical or clinical. In severe cases, the animals appear dull and apathetic and cannot stand up. Groaning and teeth grinding can also be observed. In case of a violent progression of the disease, there are signs of agitation, muscle tremors, painful pulling in of the limbs or even colic symptoms, sweating, prostrating and rolling as well as severe diarrhea with yellow-green, watery-frothy, often bloody excretions. After the previously specified symptoms, when the disease takes a severe course, the animal is down, unable to rise, apathetic, later comatose and having high heart rates of >120 beats/min. Without treatment, it can lead to the death of the animal.

Additionally, as a result of a thiamine deficiency emerging secondarily cerebrocortical necrosis can occur.

A frequent cause of rumen acidosis is a too high share of easily digestible feed ingredients (e.g. starch, sugar) such as, for instance, a too high share of concentrated feed in the total feed rations and a share of structured crude fiber that is too low. Sudden dietary changes can also lead to acidosis. As the carbohydrates gained by the degradation of concentrated feed are easily digestible, initially large amounts of short-chain fatty acids are produced in the microbial degradation of the starch. Moreover, the activity of cud chewing decreases, whereby too little of the saliva, alkaline and enriched with buffers, gets into the rumen and the rumen contents become too acidic. The composition of the microflora in the rumen is affected thereby, resulting in an increase in the microorganisms forming lactic acid and a further decline in the pH so that the fermentation to volatile fatty acids, which can be resorbed via the rumen wall and be energetically utilized by the ruminant, decreases. Lactate, in turn, accumulates in the rumen, the rumen pH drops, and the rumen wall is damaged to the point of a dissolution of the barrier function with formation of liver abscesses and other systemic manifestations (Nocek 1997; Owens, Secrist et al. 1998; Kleen, Hooijer et al. 2003; Krause and Oetzel 2006).

The term "parturient paresis" (also hypocalcemia or "milk fever") specifies a metabolism illness of lactating animals such as dairy cows. Corresponding to the name, the illness is characterized by a drop in the total calcium content in the plasma below the physiological limits of 2.3-3 mmol/l (Kraft and Dürr 2005). It occurs as subclinical hypocalcemia (calcium deficiency) around the time of calving and during early lactation. The parturient paresis occurs with an incidence of 5% (Horst, 1986), or 6-10% (Malz and Meaer, 1992). Apart from the ketosis, it is counted among the most frequent metabolism disorders (Fürll et al., 1996). Typical signs of a parturient paresis are first a reduced feed intake, agitation and nervousness, followed by a state of general weakness and dullness. Gastric activity is reduced, defecation and urination are suspended. In further stages, this is followed by the animal lying down in a position resting upright on the sternum unable to rise (downer cow), and by comatose states, which, without treatment, lead to the animal's death. (Blum u. Fischer 1974, Radostits et al. 2000; Allen and Davies 1981; Martig 2002; Oetzel 1988, Horst et al. 1997).

The clinical or subclinical hypocalcemia, furthermore, leads to dystocia, uterine prolapse, retained placenta, endometritis, infertility, mastitis, displaced abomasum, ketosis and immunosuppression (Ducusin et al., 2003, Houe et al., 2001, Kimura et al., 2006), all of which need to be addressed therapeutically.

Without wishing to be bound by theory, it is assumed that the feed supplements according to an aspect of the invention indirectly, by an improved digestion, or directly, by influencing the Ca/Mg ion conductivity of the corresponding TRP channels, cause an enhanced calcium or magnesium ion absorption or mobilization of the same. Furthermore, a correction of the alkalotic metabolism status of the ruminant should lead to a normalization of the parathyroid hormone release with the subsequent mobilization of calcium from the reserves in the bone.

The term "alleviation" can, apart from its generally accepted meaning, that is to say the alleviation of the cause and/or of the symptoms of an affliction, herein also be used in the sense of the generally accepted meanings of the term "treatment", i.e. preventing, obviating, pushing back, alleviating, improving, slowing, stopping or reversing the progression or severity of a pathological condition or of the afflictions therewith. In particular, apart from the alleviation of the cause and/or of the symptoms of a gastrointestinal tract disorder such as rumen acidosis, the treatment and prevention of the respective disorder can in this case also be comprised.

The term "feed carrier" comprises feed basic products or waters, which after being combined, complexed or aggregated with one or multiple of the TRP agonists and/or TRP antagonists according to an aspect of the present invention constitute the feed supplement or the feed according to an aspect of the invention.

Regarding the use of the TRP agonists and/or TRP antagonists of an aspect of the present invention as medicine, the term "pharmaceutical carrier" comprises inert ingredients, which after being combined, complexed or aggregated with one or multiple of the TRP agonists and/or TRP antagonists of an aspect of the present invention constitute the desired pharmaceutical formulations and are capable of releasing these TRP agonists and/or TRP antagonists again in the animal at the desired site of action (i.e. in the stomach). Accordingly, the pharmaceutical formulations of an aspect of the present invention comprise any composition that is produced by mixing a modulator of an aspect of the present invention and a pharmaceutical carrier and that can be used to alleviate the gastrointestinal illnesses, wherein the modulation of the TRP channels may be useful. Suited feed carriers or pharmaceutical carriers consist of or comprise substances from the group comprising compounds containing silicon such as wollastonite (also known as CaSiO3, or, more specifically $Ca_3[Si_3O_9]$), precipitated silicic acids, Aerosil, kieselguhr, aluminium silicates, calcium silicates, iron silicates and magnesium silicates. In addition to or instead of the compounds containing silicon such compounds which are insoluble in the gastrointestinal tract of the ruminants or of the (ruminant) tylopods and harmless in terms of nutrition physiology such as calcium sulfate dihydrate, aluminium oxides and magnesium oxides can also be used. In an embodiment, the carrier substances mentioned above are used in a highly dispersed form having a specific surface of more than 20 $m^2/g$, whereby a de-mixing of carrier substance and active substances (TRP modulators) is prevented. Without wishing to be bound by theory, it is assumed that the carrier substances here also act as an emulsifier, so that the feed supplements of an aspect of the present invention for releasing the active substances become more easily digestible. A further possibility consists in administering the substances in an oily to fatty carrier substance. Animal and vegetable fats and fatty oils (oils) can be used herein, wherein, however, vegetable fats and oils such as e.g. coconut fat and rapeseed oil are particularly suited. In an embodiment, when using oily carrier substances, the solid components are dispersed in the vegetable oil or vegetable fat used as carrier substance until an even distribution of the solid components is achieved and a de-mixing of the active and carrier substances during storage is prevented by a corresponding viscosity. Examples of the vegetable oil used according to an aspect of the invention are rapeseed oil, palm oil, soybean oil, olive oil, peanut oil, sunflower oil and wheat germ oil, and also mixtures of these oils such as e.g. a mixed oil of palm oil and coconut oil. In an embodiment, when using vegetable oil, the pharmaceutical carrier or the carrier substance comprises rapeseed oil, palm oil or soybean oil or mixtures of these oils on account of its properties in terms of nutrition physiology and processing. Examples of suited vegetable fats are coconut fat and palm fat, here particularly protected palm fat comprising saponified palm oil fatty acids (Ca soaps) and cold-spray fat as well as also mixtures of these fats. Hence, in an embodiment, the pharmaceutical carrier and/or the carrier substance comprises coconut fat or palm fat, in particular protected palm fat. Furthermore, in an embodiment, the pharmaceutical carrier and/or the carrier substance comprises mixtures of at least one of the above-named fats with at least one of the above-named oils.

The good tolerability of both the feed carrier and the pharmaceutical carrier is ensured in that only substances are chosen for this purpose which have no damaging influence when ingested by the animal.

The TRP agonist and/or antagonist can be comprised in a plant extract or derived therefrom. In an embodiment, the TRP agonist and/or antagonist is provided as an isolated active substance, for instance isolated from plant material or plant extract, or produced by chemical synthesis. On the other hand, in an embodiment, no whole plants containing the TRP agonists and/or antagonists of an aspect of the present invention are employed in the feed supplements according to an aspect of the invention in order to achieve the here-specified effects of the TRP agonists and/or antagonists for alleviating gastrointestinal tract disorders and associated systemic disorders in an animal from the suborder of the ruminants or the (ruminant) tylopods. Hence, in an embodiment, at least one of the TRP modulators is present in the feed of an aspect of the present invention as an isolated active substance.

Pellets, pressings, granulate and granular solids denote forms of feeds or feed supplements which have been reduced in volume by being compressed after the mixing of their components, whereby one can save e.g. transportation and storage capacities. Since water is also withdrawn from the feeds or feed supplements by the compression, their durability is also extended. In part, the terms can be used interchangeably, in part, however, they differ in size. Pressings (approximately 2-30 mm), granulates (approximately 0.5-3 mm) and granular solids are understood to be smaller, free-flowing particles, pellets can have a size of approximately 4 cm (each in length or diameter). Flakes likewise constitute a pressed and dried form, which, however, has more of a two-dimensional flat form in comparison to the other three-dimensional forms. In an exemplary embodiment, the feed supplements of an aspect of the present invention are formulated in such a way that the release of the TRP modulators of an aspect of the present invention takes place in the rumen. This can, for example, be achieved in that the isolated TRP modulators are embedded in a carrier substance containing fat, as defined above. An increased temperature present inside the rumen (as opposed to the surrounding temperature) leads to the release of the substances. Alternatively, the embedding of the isolated TRP modulators can take place in an acid-sensitive carrier substance, wherein the release of the TRP modulators induced by the acidic pH value present in the rumen takes place specifically in the rumen.

If not specified differently, the terms "feed supplement" or "feed additive" are herein used as equivalents and comprise substances, microorganisms or preparations which are not feed basic products or premixes and are deliberately added to feeds or water to fulfill one or multiple functions, such as e.g. the alleviation of the disorders and diseases defined herein. These functions can, alternatively, additionally and in part also adequately be selected from the group comprising: positively influencing the feed quality; positively influencing the quality of the animal products, covering the dietary requirement of the animals; positively influencing the ecological consequences of animal husbandry; positively influencing the animal production, the performance or the welfare of the animals, particularly by affecting the stomach and gut flora or the digestibility of the feeds; exercising a coccidiostatic or histomonostatic effect.

The term "disorder" is largely used as equivalent to the term "illness" or disease in the sense generally known as referring to a state of weakness, suffering or distress of a mammal caused by a malfunction of an organ, the psyche or the entire organism. Furthermore, the term "disorder" is used to specify such conditions of an organism in which the manifestation of the symptoms accompanying and characterizing the condition is weakened, whereas in an illness the symptoms are more severely manifest, up to conditions that are life-threatening for the organism. Referring to the medical nomenclature, the term "disorder" refers to a symptomatically subclinical or subacute state of weakness in an organism, whereas the term "illness" relates to a clinical, acute or even chronic debility.

DETAILED DESCRIPTION

The present invention relates in an aspect to a feed supplement for use in the alleviation of gastrointestinal tract disorders or associated systemic disorders by modulation of a Transient Receptor Potential (TRP) channel in an animal from the suborder of the ruminants (Ruminantia) or the (ruminant) tylopods (Tylopoda), containing at least one TRP agonist and/or antagonist. In particular, TRP agonists and/or antagonists according to an aspect of the invention or feed supplements containing such TRP agonists and/or antagonists are used in influencing, i.e. improving the resorption of cations in the rumen, particularly characterized in that the cations comprise ammonia and/or calcium.

Approaches to optimize the nitrogen concentration in the rumen for the microbial fermentation are currently based exclusively on an adjustment of the composition or the dosage form of the feed or on interventions into the microbial fermentation event [1-3].

However, apart from what is supplied with the food, it is also important for the nitrogen concentration in the rumen that large and varying amounts of nitrogen in the form of ammonia from the rumen get into the blood and are excreted from there via the kidney [4-6]. This constitutes a major problem in modern livestock management in two regards: for one thing, the supply of nitrogen with the food (normally in the form of expensive feed containing protein) must be increased; for another, problems arise in the disposal of the excretion products, the high nitrogen contents of which burden the environment. As a compilation from the year 2000 by the Federal Agency for Civic Education (Bundeszentrale für politische Bildung) shows, 95% of the $NH_3$ emissions come from agriculture, wherein yet again 50% of that are attributed to animal husbandry of ruminants [7].

Hitherto, it was generally assumed that the resorption event, which leads to losses of nitrogen from the rumen into the blood, is a solely passive diffusion process of the uncharged, lipophilic $NH_3$ molecule through the lipid membrane of the rumen epithelium cells. Not compatible with this notion are various transport-physiological observations on the resorption of ammonia in vivo [8] and in vitro [9].

A starting point of an aspect of the present invention was the hypothesis that in addition to the diffusion of the lipophilic form of ammonia at a physiological pH of the rumen (approx. pH 6.4) large amounts in the form of $NH_4^+$ can get into the blood via specific proteins, the nature of which makes exercising a pharmacological influence seem conceivable. This could be proved in the context of the experiments on organ preparations (isolated, fresh rumen epithelium from cattle) underlying this aspect of the invention. Herein, a conductivity induced by ammonium showed, which could be significantly influenced by application, according to an aspect of the invention, of TRP modulators such as e.g. capsaicin and menthol. As the examples 1 and 4 and FIGS. 7 to 10 show, further TRP modulators, as shown with menthol, thymol, methyl salicylate and cinnamaldehyde (also referred to as cinnamal or cinnamic aldehyde) as examples, can also be employed to influence the ammonium-induced conductivity in the rumen epithelium. The susceptibility of the protein-mediated resorption mechanisms could thus be proved and constitutes the basis for the compositions according to an aspect of the invention, which are subsequently specified in more detail.

These experiments, furthermore, support the working hypothesis with respect to the nature of the modulated protein, which is why it can be assumed that a multitude of further substances have an effect on the ammonium conductivity of the rumen (see appendix). Furthermore, it could be shown that apart from the conductivity for ammonium the resorption of calcium can also be influenced. It is to be assumed that the conductivity of further cations (particularly sodium, potassium, magnesium, protons) can also be influenced by these substances, wherein the feed supplements of an aspect of the present invention offer the property of being able to differentially regulate the resorption mechanisms for these cations in order to optimize them. In other words, according to the findings resulting from the experiments carried out according to an aspect of the invention, TRP agonists and/or antagonists are specifically used in an embodiment for influencing the conductivity of cations, in particular of ammonium and calcium ions. On account of this, the feed supplement according to an aspect of the invention is suited particularly for treating diseases and influencing the conditions of animal husbandry where the metabolism of nitrogen and calcium and/or metabolism processes that are influenced by these ions and their resorption in the rumen play a role. Hence, in an embodiment, the feed supplement of an aspect of the present invention is characterized in that it contains at least one TRP agonist and/or antagonist for influencing the resorption of cations in the rumen, wherein the cations particularly comprise ammonia and/or calcium.

In an embodiment, the at least one TRP agonist and/or antagonist is present in a concentration which (converted) essentially corresponds to that which is sufficient to influence the ammonium conductivity of isolated rumen epithelium and/or of the epithelial rumen cells according to the experiment specification in example 1 and/or 2 and/or the calcium flux across the rumen epithelium according to the experiment specification in example 4.

In an embodiment, the concentration of the at least one TRP agonist and/or antagonist is maximally 10 times, 9 times, 8 times, 7 times or 6 times higher than the calculated value, particularly maximally 5 times or 4 times, even more particularly maximally 3 times or 2 times higher than the calculated value and very particularly maximally 1.5 times higher than the calculated value or at the calculated value, in particular by taking into account the recommended amount of adding a feed supplement and the weight of the animal to be treated.

A further effect of the compositions of an aspect of the present invention results from the fact that influencing the resorption processes at the rumen will affect the composition of the rumen content, whereby impacts on the entire function of the rumen (fermentation, motor skills etc.) and of the subsequent organs (omasum, abomasum, duodenum) are to be expected with positive impacts on the animal performance.

The change in the $I_{sc}$ due to the addition of menthol and other TRP modulators mentioned in the appendix, verified in the here-specified in vitro experiments carried out with organ preparations, proves that these substances exercise an influence on the ion conductivity of the rumen epithelium. Without wishing to be bound by theory, it is assumed on the basis of these experiment results that the proteins participating in the transport processes across the rumen epithelium can be influenced by TRP modulators such as menthol, as exemplary representative of substances of the menthol type, and/or by substances of the thymol type, such as e.g. thymol or capsaicin.

The above-defined feed supplement according to an aspect of the invention is particularly characterized in that the TRP channel belongs to the group comprising TRP vanilloid 1 (TRPV 1), TRPV2, TRPV3, TRPV4, TRPV5, TRPV6, TRP Ankyrin 1 (TRPA 1), TRP melastatin 3 (TRPM 3), TRPM 5, TRPM 6, TRPM 7 and TRPM 8.

In an embodiment the feed supplement according to an aspect of the invention is characterized in that the TRP agonist and/or TRP-antagonist is present as an isolated active substance.

Herein, in an embodiment of an aspect of the present invention, the feed supplement is characterized in that the TRP agonist and/or TRP-antagonist is selected from the group consisting of capsaicin (CAS number 404-86-4), capsazepine (CAS number 138977-28-3), capsiate (CAS number 205687-01-0), capsaicinoids, menthol (CAS numbers 2216-51-5, 89-78-1, 15356-60-2, 1490-04-6), eucalyptol (CAS number 8024-53-1), resiniferatoxin (CAS number 57444-62-9), resiniferanoids, piperine (CAS number 94-62-2), piperidine (CAS number 110-89-4), camphor (CAS numbers 76-22-2, 464-49-3, 464-48-2), bis-andrographolide (5508-58-7), 2-aminoethyl-diphenylborinate, icilin (CAS number 87-08-1), olvanil (CAS number 58493-49-5), verapamil (CAS number 52-53-9, 152-11-4), quinidine (CAS number 6591-63-5), GsMTx4, St. John's wort, hyperforin (CAS number 11079-53-1), ginger (zingiber officinale; CAS number 84696-15-1), vanillylacetone (zingerone; CAS number 122-48-5), evodiamine, [6,8,10] gingerol (CAS number 23513-14-6), [6,8,10] shogaol (CAS number 555-66-8), other shogaols, cannabinol (CAS number 521-35-7), cannabidiol (CAS number 13956-29-1), cannabis, tetrahydrocannabinol (THC; CAS number 1972-08-3), other cannabinoids, polygodial (CAS number 6754-20-7), drimanial (CAS number 352311-05-8), cinnamodial (CAS number 23599-45-3), cinnamosmolide (CAS number 23599-46-4), cinnamolide (CAS number 23599-47-5), afromodial, ancistrodial (CAS number 68398-28-7), merulidial (CAS number 68053-32-7), drimenol (CAS number 468-68-8), grifolin (CAS numbers 6379-55-1, 6903-07-7), neogrifolin (CAS number 23665-96-5), albaconol, o-prenylphenol (CAS number 1128-92-3), BCTC (N-(4-Tertiarybutylphenyl)-4(3-cholorphyridin-2-yl)tetrahydro-pyrazin 1(2H)-carboxamide) (CAS number 393514-24-4), isovelleral (CAS number 37841-91-1), vanillin (CAS number 121-33-5), vanillotoxin 1, 2 and 3, arvanil (CAS number 128007-31-8), cnidarian envenomations, thapsigargin (CAS number 67526-95-8), yohimbine (CAS number 65-19-0), AG489 toxin (CAS number 128549-96-2), AG505 toxin, paradol (CAS number 27113-22-0), ginsenoside (CAS number 52286-74-5), mustard oil (CAS number 57-06-7), allyl isothiocyanate (wasabi; CAS number 57-06-7), carvacrol (CAS number 499-75-2), carveol (CAS number 99-48-9), thymol (CAS number 89-83-8), borneol (CAS numbers 464-43-7, 464-45-9, 16725-71-6, 10334-13-1, 507-70-0, 124-76-5), menthone (CAS numbers 14073-97-3, 3391-87-5, 10458-14-7), geraniol (CAS number 106-24-1), linalool (CAS numbers 78-70-6, 126-91-06, 126-90-9), menthyl lactate (CAS number 59259-38-0), p-menthane-3,8-diol (CAS numbers 3564-98-5, 3564-95-2, 42822-86-6), 1-carvone (CAS number 6485-40-1), d-carvone (CAS number 2244-16-8), isopulegol (CAS number 89-79-2), hydroxyl-citronellal (CAS number 107-75-5), allicin (CAS number 539-86-6), cinnamaldehyde (cinnamic aldehyde; CAS number 104-55-2), methyl salicilate (CAS number 119-36-8), allyl isothiocyanate (wasabi) (CAS number 57-06-7), benzyl isothiocyanate (CAS number 622-78-6), phenylethyl isothiocyanate (CAS number 2257-09-2), isopropyl isothiocyanate (CAS number 2253-73-8), methyl isothiocyanate (CAS number 556-61-6), prostaglandin (PGA1 14152-28-4, PGB1 13345-51-2, PGC1 35687-86-6, PGD1 17969-82-0, PGE1 745-65-3, PGE2 363-24-6, PGF1α 745-62-0, PGG2 51982-36-6, PGH3 60114-66-1, PGA2 13345-50-1, PGB2 13367-85-6, PGD3 71902-47-1, PGF2α 551-11-1, PGF2β 4510-16-1, PGC3 52590-97-3, PGI2 35121-78-9), prostaglandin synthesis inhibitors, acetylsalicylic acid (CAS number 50-78-2), paracetamol (CAS number 103-90-2), ibuprofen (CAS number 15687-27-1) and warburganal (CAS number 62994-47-2). The CAS numbers have been specified here as international identification numbers for the respective substance and, where applicable, for the various isoforms in brackets after the substance. With the help of the number, the individual substances and their formulas can be identified and checked in free databases, e.g. at chemsub.online.fr/ or on reference websites such as en.wikipedia.org.

The results illustrated in the examples, particularly in the examples 1 and 4, and FIGS. 1, 2 and 7 to 10, prove that according to an aspect of the invention the conductivity and/or the resorption of cations across the rumen epithelium can be modulated by TRP modulators. Here, a distinction is made between different active profiles, which can lead to effects of different uses on the entire organism and on account of which the TRP modulators of an aspect of the present invention are classified and can be employed as follows:

TRP Modulators Causing the Increase of the Cation Resorption (Type "Menthol"):

Without wishing to be bound by theory, it is assumed on account of the results presented here that the substances with the active profile presented here with menthol as an example (menthol-type active profile) are especially suited to influence the conductivity of the rumen epithelium for cations and thus, for example, to improve the resorption of calcium and/or magnesium, to increase the resorption of protons from the rumen and/or to increase the resorption of ammonium from the rumen. Hence, in an embodiment, the feed supplements of an aspect of the present invention contain substances with the menthol-type active profile in order to modulate the conductivity of the rumen epithelium for cations. In an embodiment, the feed supplements of an aspect of the present invention contain substances of the menthol-type active profile to improve the resorption of calcium and/or magnesium, to increase the resorption of protons from the rumen and/or to increase the resorption of ammonium from the rumen.

Allocating the substances to one of the two mentioned types of active profile, i.e. to the menthol type or to the thymol type, is with respect to the TRP modulators of an aspect of the present invention for instance done on the basis of their suitability for achieving the effects on the resorption of ammonium, calcium, magnesium and/or protons from the rumen which are specified above and below for the respective types of substances. Substances showing the same active profile as it is shown in relation to these effects in the examples for menthol are allocated to the menthol type, substances showing the same active profile as it is shown in relation to these effects in the examples for thymol are allocated to the thymol type.

In an embodiment, as component of the feed supplements of an aspect of the present invention, substances from the group comprising menthol, menthone, eucalyptol and geraniol, particularly consisting of menthol, eucalyptol and menthone, are here employed as substances with the menthol-type active profile. Particularly, menthol is employed as component of the feed supplements of an aspect of the present invention as the substance from the menthol active profile type.

On account of the suitability of the substances of the menthol active profile type for increasing the absorption of cations from the rumen and the resulting rise in the blood concentration of magnesium and calcium and/or increasing the absorption of ammonium from the rumen and a resulting rise in the rumen pH, there is a special suitability of the feed supplements of an aspect of the present invention containing the TRP modulators of the menthol active profile due to their suitability for preventing and/or alleviating the parturient paresis/grass tetany and/or preventing and/or alleviating the rumen acidosis. Hence, in an exemplary embodiment, the feed supplements of an aspect of the present invention containing TRP modulators of the menthol active profile, especially menthol, are employed for preventing and/or alleviating the parturient paresis/grass tetany and/or the rumen acidosis. A drawback of the exclusive use of TRP modulators of the menthol type of an aspect of the present invention could, however, lie in a deterioration of the nitrogen utilization due to losses of ammonium from the rumen.

TRP Modulators Causing the Inhibition of the Cation Resorption (Type "Thymol"):

Without wishing to be bound by theory, it is assumed on account of the results presented here that the substances with the active profile presented here with thymol as an example (thymol-type active profile) are especially suited to inhibit the resorption of ammonium from the rumen and/or to improve the resorption of calcium and/or magnesium.

Hence, in an embodiment, as component of the feed supplements of an aspect of the present invention, substances with the thymol type active profile are employed to inhibit the resorption of ammonium from the rumen and/or to improve the resorption of calcium and/or magnesium. In an embodiment, as substances with the thymol type active profile, substances from the group comprising: thymol, cinnamaldehyde (cinnamic aldehyde), methyl salicylate, carvacrol, eugenol and mustard oil are employed, particularly consisting of thymol, methyl salicylate, and cinnamaldehyde, particularly consisting of thymol. With respect to the mustard oil, allyl isothiocyanate is employed supplementary or alternatively as a suited component.

On the basis of the experiment results specified here, it could be shown that the exemplary TRP modulators of an aspect of the present invention, thymol, cinnamaldehyde and methyl salicylate have a similar active profile in the forestomach system, specifically the rumen. Thymol is a TRPV3 agonist. Cinnamaldehyde and methyl salicylate are both potent TRPA1 agonists, to which carvacrol, eugenol and mustard oil (one active substance of which is allyl isothiocyanate) also belong; see also table 4 on pages 90-91 in Vriens, Nilius et al., Curr Neuropharmacol 6 (2008), 79-96, the disclosure of which is hereby incorporated by reference into the present application.

Menthol, a further exemplary TRP modulator of an aspect of the present invention, however, showed a different active profile. Menthol is considered to be a potent TRPM8 agonist, as are menthone, eucalyptol and geraniol (see table 3 in Vriens, Nilius, et al. (2008); vide supra; the disclosure of which is hereby incorporated by reference into the present application).

However, the effect of these substances can, also on account of their complex binding and modulating behavior with respect to further TRP channels, also be different on different organs.

Menthol, for instance, likewise belongs to the TRPV3 agonists, however, the experiments carried out with this TRP modulator and specified in the examples showed an opposite effect compared to thymol (likewise a TRPV3 agonist) in experiments on the rumen. This indicates that a TRPM8-specific effect occurs, mediated by menthol, and/or that it predominates over the TRPV3-mediated one. Eugenol, in addition to being an TRPM8 agonist, also belongs to the TRPA1 and TRPV3 agonists and is hence allocated to the thymol type, since the active profile specified here has already been verifiably shown for both TRPA1 (cinnamaldehyde) and TRPV3 agonists (thymol).

The results, which are here specified in the context of an aspect of the present invention with respect to menthol, thymol, cinnamaldehyde and methyl salicylate as well as the existing literature can also be used to allocate the additionally mentioned suited TRP modulators of an aspect of the present invention to the two aforementioned modulator types.

Without wishing to be bound by theory, it is assumed that
  TRP modulators showing behavior similar to the one specified here for menthol, i.e. particularly have a TRPM8 agonistic effect, can be allocated to the menthol type.
  TRP modulators showing behavior similar to the one specified here for thymol, cinnamaldehyde and methyl salicylate, i.e. particularly activating TRPV3 and/or TRPA1 but not TRPM8, can be allocated to the thymol type. Likewise, TRP modulators that activate TRPV3, TRPA1 and TRPM8, such as e.g. eugenol, can accordingly also be allocated to the thymol type.

A further specific property of the feed supplements of an aspect of the present invention containing the TRP modulators of the thymol active profile results from their suitability for improving the protein utilization by reducing the absorption of ammonium from the rumen into the blood and by a rise in the ammonium concentration in the rumen and an increased integration of nitrogen into microbial protein resulting therefrom, which, consequently, also results in a reduction of the nitrogen emission into the environment. Furthermore, the results presented in the examples show the suitability of the TRP modulators of the thymol type for preventing and/or alleviating states of disease characterized by hypocalcemia such as parturient paresis or by hypomagnesemia such as in grass tetany due to the increased resorption of calcium and/or magnesium caused by them. Hence, in an exemplary embodiment, the feed supplements of an aspect of the present invention containing TRP modulators of the thymol active profile, especially thymol, are employed to improve the protein utilization and/or to prevent and/or alleviate the parturient paresis/grass tetany. The feed additives of an aspect of the present invention containing the TRP modulators characterized here, which cause an increased calcium conductivity of the rumen epithelium and/or an increased calcium resorption, are employed in the prevention or alleviation of this disease in all stages of a hypocalcemia. Analogously, the feed additives of an aspect of the present invention containing the TRP modulators characterized here, which cause an increased magnesium conductivity of the rumen epithelium and/or an increased magnesium resorption, are employed in the prevention or alleviation of this disease in all stages of a hypomagnesemia.

Mixtures of the Above-mentioned Substance Types:

According to the results shown in the examples, with the combination of substances of the menthol/thymol type, particularly a combination of menthol and thymol themselves, an optimal action principle might be attainable, combining the properties and largely avoiding the drawbacks of the use of the respective substance active profile type, that is, as explained above, e.g. stimulating the calcium and/or magnesium resorption, preventing and/or alleviating the parturient paresis and/or grass tetany and/or rumen acidosis and/or inhibiting the ammonium resorption/improving the nitrogen utilization and along with that largely avoiding the deterioration of the nitrogen utilization due to losses of ammonium from the rumen.

Here, it proves to be a specific property of the use of such combination preparations, i.e. feed supplements containing TRP modulators of both types of active profile, that is of the menthol and the thymol type, that thymol apparently acts selectively inhibiting on the transport of univalent cations (ammonium) without interfering with divalent cations ($Ca^{2+}$ and $Mg^{2+}$).

In an embodiment, herein the feed supplements of an aspect of the present invention particularly contain at least one TRP modulator from each of the two active profile types selected from the group comprising menthol, menthone, thymol, carvacrol, geraniol, cinnamaldehyde, eugenol, mustard oil, citral, and eucalyptol, particularly from the group comprising menthol, menthone, thymol, carvacrol, geraniol, eugenol and cinnamaldehyde, even more particularly from the group comprising menthol, menthone, thymol, carvacrol and eugenol, and very particularly from the group comprising menthol and thymol. In an embodiment, here, at least one of the TRP modulators is present in the feed of an aspect of the present invention as an isolated active substance.

In an embodiment, in the production of the feed supplements of an aspect of the present invention, the TRP modulators of the above-mentioned active profile types are mixed together at a proportion ratio menthol type to thymol type of 1:10 to 10:1; particularly at a proportion ratio menthol type to thymol type of 1:3 to 3:1; and very particularly at a proportion ratio menthol type to thymol type of 1:1 to 2:1.

In an embodiment, in the production of the feed supplements of an aspect of the present invention, a daily amount or dosage of the TRP modulators of the menthol active profile type is chosen here in the amount of 10 to 3000 mg/kg dry matter (DM) of the concentrated feed (CF), particularly 20 to 500 mg/kg DM CF (without carrier substance), more particularly 22 to 333 mg/kg DM CF (without carrier substance), even more particularly 22 to 222 mg/kg DM CF (without carrier substance) and very particularly 56 to 166 mg/kg DM CF. In an embodiment, menthol is employed herein as the most suited representative of the substances of the menthol active profile type.

In an embodiment, in the production of the feed supplements of an aspect of the present invention, a daily amount or dosage of the TRP modulators of the thymol active profile type is chosen here in the amount of 10 to 3000 mg/kg dry matter (DM) of the concentrated feed (CF), particularly 10 to 500 mg/kg DM CF, more particularly 11 to 167 mg/kg DM CF, even more particularly 11 to 111 mg/kg DM CF and very particularly 28 to 84 mg/kg DM CF (each without carrier substance). In an embodiment, thymol is employed herein as the most suited representative of the substances of the thymol active profile type.

In feed supplements of an aspect of the present invention which contain TRP modulators of both active profile types, in an embodiment, a daily total amount or dosage of the TRP modulators of both active profile types of 20 to 6000 mg/kg dry matter (DM) of the concentrated feed (CF) is chosen, particularly 20 to 1000 mg/kg, more particularly 20 to 500 mg/kg DM CF, even more particularly 33 to 333 mg/kg DM CF and very particularly 83 to 250 mg/kg DM CF (each without carrier substance). In an embodiment, menthol as the most suited representative of the substances of the menthol active profile type and thymol as the most suited representative of the substances of the thymol active profile type are employed herein.

In an embodiment, the present invention hence provides in an aspect a feed supplement for influencing the resorption of cations such as, for example, ammonium, calcium and magnesium in the forestomach system of the ruminants (Ruminantia) or the (ruminant) tylopods (Tylopoda), containing at least one Transient Receptor Potential TRP channel modulator from the group of the TRP agonists and/or antagonists, wherein particularly a tolerable feed carrier is comprised.

Some of the above-mentioned substances or plant extracts containing such substances have already been examined in previous studies. The international patent application WO 2011/153299 A2, for example, specifies the feeding of the oregano plant or extracts thereof to influence the fermentation process by influencing the digestion processes in cattle with the aim of reducing methane production. No indication, however, can be found of a change of the resorption mechanisms of the rumen epithelium for ammonia or ammonium or for other ions.

The application US 2009/0004308 A1 specifies the administration of benzoic acid to poultry as feed additive together with a mixture of at least two substances from the group consisting of thymol, eugenol and piperine, which are present in plant extracts or in the corresponding plants themselves, which is meant to lead to a better digestion and a faster weight gain in the animals. However, no disclosure can be found of effects of such a supplementary feeding on the digestion of ruminants, which in terms of the digestion process are fundamentally different from poultry.

Ando et al. (2003) specify the supplementary feeding of peppermint in cattle. They observe a slightly improved digestive event in the animals thus fed, however, likewise without any indication of a change of the resorption mechanisms of the rumen epithelium for ammonium or for other ions. Furthermore, they also observe a decrease in the rumen pH in the animals supplementary fed with herbs, which would constitute a contraindication of this supplementary feeding in the treatment of rumen acidosis. In contrast to the methods and feeds presented there, the present invention aims in an aspect at an undisturbed fermentation event while at the same time influencing the resorption.

The concentrations of TRP agonists and/or antagonists employed according to an aspect of the present invention lie in a very low dosage range. There are various in vitro and in vivo studies in the literature, which prove that with the substances and dosages suited according to an aspect of the present invention the microorganism composition and the fermentation performed by the microorganisms are not influenced.

Thus, for instance, Evans and Martin (Curr Microbiol 41 (2000), 336-340) could detect no effect on the bacteria flora in the ruminal fluid in in vitro studies with thymol amounts of 3-12 g/60 l. Macheboeuf et al. (Anim. Feed Sci. Technol. 145 (2008) 335-350), when employing 1.5 mM thymol (corresponding to 14 g/60 l ruminal fluid), could observe no influence on the methane, ammonium, acetate and propionate production, which could be used as indicators of possible changes in the bacteria flora. Only at very high concentrations starting at 500 mg/l (corresponding to 30 g/60 l) were Castillejos et al. (J. Dairy Sci. 89 (2006), 2649-2658) able to see a significant influence on the pH, the $NH_3$ concentration and the production of volatile fatty acids (VFA).

Similarly, there are also no indications in the literature that high doses of menthol would have an effect on the microorganism composition and the fermentation performed by the microorganisms. So even when employing 0.3% menthol in relation to the feed dry mass (equivalent to 8 g menthol/day) for 30 days in bulls, no influence on the amount of *E. coli* in the feces of the animals could be observed (see last section on page 139 of the dissertation "*Factors influencing Escherichia Coli* O157 *colonization of the gastrointestinal tract of feedlot cattle*" by Celine C. Aperce at the Kansas State University from 2012). When employing menthol as a component in peppermint (peppermint oil) at 9 g/60 l ruminal fluid, Agarwal et al. (Anim. Feed Sci. Technol. 148 (2009), 321-327) were indeed able to observe that the methane production was reduced, however, without the production of volatile fatty acids or the bacteria composition having been influenced.

Hence, on the basis of the here-specified TRP modulators and their dosages, it is to be assumed that when feeding the feed supplements according to an aspect of the invention the microorganism composition and the fermentation performed by the microorganisms are not influenced. Hence, in an embodiment, the feed supplements according to an aspect of the invention do not influence the microflora in the intestines of the ruminants or tylopods.

In contrast, in the experiments carried out in the context of an aspect of the present invention it was detected that the resorption behavior in ruminants and (ruminant) tylopods can be changed by modulation of the TRP channels by means of TRP agonists and/or antagonists such as, for instance, menthol as the representative of substances of the menthol type and/or substances of the thymol type, e.g. thymol, capsaicin, cinnamaldehyde or verapamil, in such a way that due to the changed ion flow the resorption of ammonium and of other ions changes, and thus it is possible to counteract the development of disorders which are based on, for instance, an increased ion concentration in the gastrointestinal tract.

In an embodiment, the feed supplement according to an aspect of the invention is characterized in that a tolerable feed carrier is comprised.

Herein, any kind of feed fed to ruminants can be used, e.g. feeds which comprise a component of grass, vegetables, corn or small grain silage or hay, grain byproducts, oilseeds or oilseed flours, corn kernels and small grains and so forth in order to provide a supplementary feed.

The added amount of the feed supplement according to an aspect of the invention can herein vary per capita per day, depending on the administration and the species to be fed.

In general, the feed supplement according to an aspect of the invention is characterized in that the TRP agonist and/or TRP-antagonist is employed in a concentration range of 0.01 to 10 g/kg feed.

Depending on which TRP channels are to be modulated and how this modulating shall turn out with respect to the respective TRP channels, it can be suited to combine two or multiple TRP modulators in a feed supplement instead of only one. The feed supplement according to an aspect of the invention can in such cases contain 2, 3, 4, 5, 6, 7, 8, 9, 10 or more TRP agonists; 2, 3, 4, 5, 6, 7, 8, 9, 10 or more TRP antagonists; or 2, 3, 4, 5, 6, 7, 8, 9, 10 or more TRP modulators, as listed in tables 10 to 13, of which some are TRP agonists, others TRP antagonists. Some of the modulators have different effects in relation to different TRP channels. Menthol, for example, is an antagonist of the TRPA1 ion channel, however, an agonist of the TRPM8 ion channel at the same time also. Other TRP modulators, such as e.g. ginger, can influence multiple TRP channels, among them e.g. TRPV3 (see table 13). Depending on the intended effect 2, 3, 4, 5, 6, 7, 8, 9, 10 or more TRP modulators, as listed in the tables 10 to 13, can be contained in a feed supplement according to an aspect of the invention. In an embodiment, the feed supplement defined above is characterized in that the feed supplement contains at least two or more TRP agonists and/or TRP antagonists. In an embodiment, the feed supplement defined above is characterized in that the feed supplement contains at least one TRP modulator of the menthol type and/or of the thymol type, wherein particularly menthol is the TRP modulator of the menthol type, and thymol is the TRP modulator of the thymol type.

As explained above, the feed supplements of an aspect of the present invention can generally be employed for an improved feed utilization resulting from an improved digestion, for changing the gas composition produced herein, particularly for decreasing the ammonium production as well as, in the case of gastrointestinal tract disorders and/or associated disorders/illnesses, also for alleviating such a disorder/disease.

Hence, the present invention also provides in an aspect a feed supplement as defined above, characterized in that the gastrointestinal tract disorders or the associated systemic disorders can be alleviated which belong to the group comprising movement disorders of bonnet and the rumen; disorders in the forestomach passage; bonnet and rumen inflammation; Hoflund syndrome; fermentation disorders; subacute rumen acidosis; subclinical rumen acidosis; clinical rumen acidosis; acute rumen acidosis; displaced abomasum; laminitis; liver abscesses; ulcers; rumen alkalosis; septic fermentation; rumen tympanites; diseases of the oral cavity and pharynx; diseases of the omasum, abomasum, small intestine and large intestine; hypomagnesemia/grass tetany; hypocalcemia/parturient paresis. It is in particular possible that the gastrointestinal tract disorder or the associated systemic disorder comprises rumen acidosis and parturient paresis.

TRP agonists and/or antagonists as well as feed supplements containing such TRP agonists and/or antagonists according to an aspect of the invention are likewise characterized in that, apart from alleviating the above-specified gastrointestinal tract disorders or the associated systemic disorders, they are suited to also be employed leading over to the treatment of the corresponding illness, should, for example, the condition of the animal concerned at first deteriorate, or they can also be employed directly for the alleviation of the corresponding illnesses, i.e. the gastrointestinal tract illnesses of the same name and/or the associated systemic illnesses. The terms disorder and illness are in this context therefore used as equivalents with regard to the possibilities for application of the TRP modulators according to an aspect of the invention for their alleviation.

The feed supplements according to an aspect of the invention are initially thought to be employed in commercial animal breeding and/or husbandry, nonetheless, they can be employed both in domesticated and in wild animals also.

In an embodiment, the above-defined feed supplement is provided, wherein the animal belongs to the group comprising cattle, sheep, goats, giraffes, yaks, red deer, fallow deer, moose, roe deer, antelopes, buffalo, bison, Bactrian camels, dromedaries, alpacas, llamas, guanacos and vicuñas.

The administration of feed supplements according to an aspect of the invention can take place in addition to the feeds provided for the animals, e.g. in the form of a premix that is mixed into the respective feed prior to, during or shortly after the distribution of the feed to the animals. As nowadays the feeds are often already acquired and employed by the animal holders as ready-made mixtures, the feed supplements according to an aspect of the invention can likewise already be added to these ready-made mixtures. For this reason, in an embodiment, the feed supplement as defined above is provided, which is characterized in that the feed supplement is mixed into a feed.

The present invention relates, furthermore, in an aspect to a method for producing a feed or feed supplement, characterized in that it comprises the steps:
(a) Providing a basic composition of a feed or feed supplement;
(b) Mixing in a feed supplement and/or at least one TRP agonist and/or TRP antagonist as defined above; and
(c) Formulating the obtained mixture as feed or feed supplement.

In an embodiment, this method according to an aspect of the invention is characterized in that the basic composition essentially consists of a commercially available concentrated cattle feed, into which the feed supplement according to an aspect of the invention is mixed. An approximate composition of such a feed is listed in table 9, in the appendix. This composition is given only as an example. The feed composition can vary depending on the intended use. In feed for fattening, (calf-) breeding feed or dairy feed, for example, crude fat and/or vitamin/mineral nutrient premixes can be added also, and the individual shares in the total amount can vary (e.g. crude protein share between approximately 15 and 40%, crude fibre share between approximately 7 and 20%, crude fat share between 2 and 6%, etc.). Specific exemplary cattle feed compositions can, for example, be taken from the patent application DE 102006026512 A1, on page 3, section 19, there specified as maintenance feed or feed for fattening, the disclosure of which is hereby incorporated by reference into the present application.

The TRP modulators can be employed in various forms in the above-specified method according to an aspect of the invention, comprising the plants or organisms in which they are found or are enriched, extracts therefrom, isolated and/or synthesized active substances. In an embodiment, the method defined above is provided, characterized in that at least one TRP agonist and/or TRP antagonist is mixed in as an isolated active substance.

The present invention also relates in an aspect to feeds containing a feed supplement according to an aspect of the invention or the at least one of the above-mentioned TRP modulators, and/or to feeds obtainable by the method specified above.

One of the special properties of an aspect of the present invention is that due to the experiments underlying an aspect of the invention it is possible to define the individual substances which are suited to achieve the object specified above. Therefore, it is not necessary to feed plant parts containing these substances to the animals, but instead it is now possible to administer the individual substances, which were identified as active substances, and thus to amplify the effect achieved by them, or even only to let it become evident by isolating them from potentially interacting substances. Hence, in an embodiment, the feed according to an aspect of the invention or the feed additive as defined above is provided by an aspect of the present invention, characterized in that at least one TRP agonist and/or TRP antagonist is present in an increased concentration, measured in relation to its content in raw plant material or a plant extract.

The feed or feed supplement according to an aspect of the invention can be formulated in various forms, which are known and common in the feeding of animals. In an embodiment, the feed or feed supplement as specified above is provided, characterized in that the feed or the feed supplement is present in the form comprising pill, pellet, coated pellet, flake, granulate, pressing, granular solid, coated tablet, solution, powder, in a pouch, component in a mineral lick or as drop.

Furthermore, the present invention also relates in an aspect to the use of a TRP agonist and/or TRP antagonist as defined above in the production of feeds, feed supplements, feed additives or drink supplements.

According to an aspect of the invention, in acute or severe gastrointestinal tract disorders and/or the associated systemic disorders, TRP modulators can also be employed as a medicine and, for example, be administered only after the symptoms of the disease occur. For this reason, in a further embodiment, the present invention provides in an aspect the TRP agonist and/or TRP antagonist as defined above for use as medicine in the treatment of gastrointestinal tract disorders or the associated systemic disorders. Here, also, the TRP modulators according to an aspect of the invention are suited to serve as medicine in the treatment of the corresponding gastrointestinal tract illnesses and/or the associated systemic illnesses.

In summary, the present invention relates in aspects to the feed supplements, feeds and TRP modulators, i.e. TRP agonists and TRP antagonists, which are specified above and illustrated in the examples, for or in the modulation of the speed with which cations from the rumen are resorbed in an animal from the suborder of the ruminants or the (ruminant) tylopods and/or for increasing the integration of ammonia into microbial protein utilizable for the animal.

These and other embodiments are disclosed and comprised by the specification and the examples of aspect of the present invention. Further information regarding materials, methods, procedures, materials and substances, which are to be employed according to the teachings of an aspect of the present invention, can be taken from documents that are accessible in or by means of public libraries and databases. In this regard, for example, the online database "Medline", provided by the National Center for Biotechnology Information and/or the National Library of Medicine at the National Institutes of Health, can be used. Further databases and internet addresses are known to the average person skilled in the art or can be found with the help of internet search engines.

General information with respect to the symptomatology and treatment of animal and livestock diseases can be taken from standard works of veterinary medicine, some of which are presented hereafter as examples: Dirksen, G.; Gründer, H. D.; Stöber, M.; 2002 Innere Medizin and Chirurgie des Rindes. Parey in Blackwell Verlag GmbH, Berlin-Wien; Hartmann, H.; Meyer, H.; 1994 Klinische Pathologie der Haustiere. Gustav Fischer Verlag, Jena, Stuttgart; Hoffmann, W.; 1992 Rinderkrankheiten. Vol 1. Innere and chirurgische Erkrankungen, Verlag Eugen Ulmer, Stuttgart, 304-305; Kraft, W.; Dürr, U. M.; 2005 Klinische Labordiagnostik in der Tiermedizin. Schattauer.

General information with respect to the diet of ruminants and to feeding strategies can also be taken from a multitude of standard works and articles published by state and private institutions, some of which are presented hereafter as examples: Kirchgessner, M.; 2004 Tierernährung. DLG Verlag, Frankfurt am Main; Jeroch, H.; Drochner, W.; Simon, O.; 1999 Ernährung landwirtschaftlicher Nutztiere. Verlag Eugen Ulmer Stuttgart; Hoffmann, M. H.; 1990 Fütterungsregime für Rinder in Tierfütterung, vol 2. ed. Dt. Landwirtschaftsverlag, Berlin, 3485; Piatkowski, B.; Giirtler, H.; Voigt, J.; 1990; Grundzüge der Wiederkäuerernährung. Gustav-Fischer-Verlag, Jena-Stuttgart, 236 p; Steinwidder, A.; 2005 Milchviehfütterung: Tier- and leistungsgerecht. Stocker, 240 p.

The specification above represents a general disclosure of aspects of the present invention. A multitude of publications have been cited herein. A complete list of references is located at the end of the specification, directly before the claims. The disclosure of all the publications cited (including the scientific literature, the granted patents, the published patent applications, specifications and instruction manuals from the manufacturers, and so forth) is hereby explicitly incorporated by reference into the present application.

A more detailed understanding of aspects of the present invention can be gained from the following specific examples, which are attached for this purpose only, however, and are in no way intended to restrict the scope of the invention.

EXAMPLES

Materials and Methods
Study Material
Organ preparations:
Freshly isolated rumen epithelium
From cattle (normally from slaughterhouses in the area)
From sheep (material from the Department of Veterinary Medicine (FB Veterinärmedizin) Berlin)
From camel (collaboration with partners from Sudan/Saudi Arabia)
Isolated and cultivated cells from the tissues mentioned above Obtaining, Preparing and Transporting the Epithelium The animals are stunned with a captive bolt gun and killed by the subsequent blood withdrawal. The rumen is taken out along the slaughter line by the slaughterhouse personnel and submitted for obtaining the epithelium (cattle) or taken out by the examiners on site (sheep).

The extraction of the piece of rumen epithelium with a size of approx. 10 cm$^2$ takes place from the ventrolateral region (ventral rumen sac atrium passage) of the rumen. In order to remove coarse feed components, the obtained epithelium is rinsed with plenty of transport buffer solution (composition see table 1) and thereafter freed of the fat and muscle layer by "stripping".

Transport and storage of the experiment take place in the transport buffer solution (table 1), which is temperature-controlled (37° C.), gassed with carbogen (95% $O_2$ and 5% $CO_2$) and set to a pH value of 7.4.

Isolating the Cells

Isolating the cells takes place according to established methods (fractional trypsinization (Galfi, Neogrady et al. 1981; Schweigel, Lang et al. 1999)). For this purpose, the villi of the freshly retrieved epithelium are taken off and, while stirring, incubated in DPBS buffer solution without $Ca^{2+}$ and $Mg^{2+}$ (Dulbecco's PBS+EDTA+4% penicillin-streptomycin (10 000 U·ml-l/10 000 µg·ml-l) (Biochrom AG, Berlin, Germany), to which 0.25% Trypsin-EDTA (Sigma-Aldrich, St. Louis, Mo., USA) is added. After incubation (about 45 minutes), the cells of the top cell layer (Stratum corneum) start to come off. By filtration (sterile gauze), the cell suspension is separated from the tissue material, which is again incubated in fresh solution. This procedure is repeated until the round cells of the Stratum basale show themselves in the supernatant, which cells are separated by centrifugation from the remaining cell material and seeded in collagenized dishes (collagen A) with M199 cell culture medium with 150 ml·l$^{-1}$ fetal calf serum, L-glutamine (6.8 mmol·l$^{-1}$), nystatin (2.4·105 U·l$^{-1}$), gentamycin (50 mg·l$^{-1}$), and kanamycin (100 mg·l$^{-1}$) (Biochrom AG, Berlin, Germany or Sigma-Aldrich, St. Louis, Mo., USA). After establishing the culture, a switch to DMEM medium (Pan Biotech GmbH, Eidenbach, Germany; with 4.5 g·l$^{-1}$ glucose, 3.7 g·l$^{-1}$ NaHCO3, and L-glutamine) with 10% fetal calf serum, HEPES (2%), and penicillin/streptomycin (1%) takes place. After reaching confluence, the seeding onto cover slips takes place on the day of the experiment itself or on the day prior to the experiment.

Experiments on the Intact Epithelium

The experiments on the intact epithelium take place as already specified (Abdoun, Stumpff et al. 2005; Abdoun, Stumpff et al. 2010). The measuring techniques used are a combination of the Ussing chamber technique developed by Ussing (1949) and the microelectrode technique.

Electrophysiological Measuring by Means of the Ussing Chamber

When examining epithelial transport processes with the Ussing chamber, the epithelium is installed in a special chamber, which makes it possible to rinse the two sides of the epithelium (apical: food side; basolateral: blood side) separately of each other with buffer solutions of various composition, wherein the electrophysiological parameters (current and voltage) across the epithelium are traced. Hereby, it is made possible to differentiate between the transport of an uncharged substance (e.g. ammonia, $NH_3$) and the transport of a charged substance (e.g. ammonium, $NH_4^+$), as the former takes place without a change in current and voltage, whereas the latter is coupled with the transfer of a charge and thus changes the transepithelial electrical parameters.

Herein, the simultaneous registration of the electrophysiological parameters of up to 24 different pieces of epithelium of the same animal is carried out, wherein the test solutions can be selected at will.

With the help of a special modification, the reaction of individual epithelia to solution changes, taking place very rapidly and smoothly, is also examined over time. Hereby, for example, the reproducibility of a pharmacological intervention on the same piece of epithelium can very well be examined. This modification of the classic Ussing chamber technique is particularly, albeit not exclusively, used for the comparative "screening" of the various substances which are subject of an aspect of the present invention. In addition to this test of which substances have an effect on transport processes, the Ussing chamber is, hence, also employed to, for example, characterize the dose at which measureable effects are to be expected, and/or to characterize the transported ion species which is influenced by the respective test substance.

Measuring the Transport ("Flux") by Means of the Ussing Chamber

Supplementary, the transport rate of a substance across the epithelium is quantitatively determined by examining the buffer solution prior to and after a defined test period (in conjunction with the methods of an aspect of the present invention for determining the ammonia flux by means of an ammonia electrode (Thermo Scientific Orion 9512HPB-NWP, Thermo Fisher Scientific Inc., Waltham, Mass. 02454) while at the same time registering shifts in the solution pH, or measuring the calcium flux with radioactive isotopes).

Measuring the Intracellular Parameters by Means of a Microelectrode (Apical Potential and Intracellular pH)

During the individual experiments a microelectrode is inserted into the epithelium in order to register the cell membrane potential and the intracellular pH value of the cell simultaneously with the electrophysiological parameters. Hereby it is possible to make a distinction whether an ion is transported paracellular (that is, between the cells) or transcellular (that is, through the cells). The changes in the membrane potential suggest that the transport takes place transcellularly via ion channels.

This method is rather time-consuming in terms of the experiments and is, for this reason, employed for a closer characterization of reactions which attract attention when screening the substances in the electrophysiological measurement by means of the Ussing chamber.

Registering the Transepithelial Electrophysiological Parameters

The epithelium is horizontally clamped into a modified Ussing chamber, wherein the mucosal side faces upwards. The chamber made of plexi-glass has a cross-section surface of 0.79 cm$^2$, which is corrected to 1 cm$^2$. As a protection against damages on the edges of the epithelium, "edge damage", a silicone ring is in each case placed between chamber and epithelium. The two resulting chambers (mucosal and serosal) are each supplied by their own perfusion system (4-channel-stand-pump, Ismatec SA). With three-way valves, an independent solution change between altogether eight solutions is possible in the two chambers. During storage, the solutions are gassed in their containers with 100% $O_2$. To warm the solutions up to 37° C., the thin perfusion tubes run through a heat exchanger pump. The suction device (Masterflex R/S, Cole Parmer Instrument Company) present in both chambers guarantees a rapid and safe change of solution. In order to ensure that there are no solution change artefacts when adding agonists and antagonists, the substances are pipetted into the respective solution, wherein the gassing ensures a rapid mixing. In this way, pressure fluctuations or an interruption of the flow through the chamber can be safely precluded.

As in the conventional Ussing chamber technique, there are in each case two electrodes near the tissue and two electrodes distant from the tissue for measuring the transepithelial potential difference and the transepithelial current ($I_{sc}$). The connections between the Ag/AgCl electrodes, which are filled with 3 M KCl, are established via agar bridges. Just as in Strecker (Strecker 2011), the measuring chamber is connected to a "voltage clamp" installation (Ussing chamber unit) in assembly with a microelectrode amplifier (both Biomedical Instruments Co., Germering). A micromanipulator (MF 500) installed above the measuring chamber offers the possibility to move the microelectrode in fine µm steps. Additionally, a microscope as well as a cold-light source are located above the apparatus.

Measurement with "Double Barreled" Microelectrodes

The double barreled microelectrode is made of two borosilicate capillaries. A channel serves for measuring the apical membrane potential difference and is filled with 0.5 M KCl. The other channel serves for measuring the intracellular pH value. This channel initially gets a hydrophobic coating by silanization with dichloromethylsilane (Sigma-Aldrich). After filling in a liquid ion exchanger (hydrogen-ionophore I Cocktail A; Fa. Sigma-Aldrich), a liquid membrane forms, and with that a solid connection of the ion-selective ionophore to the glass capillary. This ionophore used is selective for $H^+$ ions, which means that solely these ions can be transported via the ionophore to the "back-fill solution" and lead to a change in potential that is proportional to the existing $H^+$ concentration. This measured potential must be corrected by the value of the apical membrane potential, which is made possible by the measurement by means of the reference electrode. The two capillaries are connected to a high-impedance microelectrode amplifier (F-223 A Dual Electrometer, WPI) via freshly chlorinated silver wires. This high-impedance microelectrode amplifier in each case measures the potential present above each of the two capillaries. Forming the voltage difference results in a linear function of the $pH_i$ (intracellular pH value).

By employing a combination of double barreled microelectrodes and an Ussing chamber, in addition to transepithelial Ussing chamber measurement data (such as $PD_t$, $I_{sc}$, transepithelial conductivity), intraepithelial measurement data such as $PD_a$ and $pH_i$ are also registered if required (Strecker 2011).

Test Solutions

In detail, the test solutions used can be taken from the tables in the appendix.

Menthol (Sigma-Aldrich) was dissolved at a concentration of 1 mol·l$^{-1}$ in ethanol and pipetted into the used test solution containing ammonium. For an end concentration of 1 mmol·l$^{-1}$, 20 µl of this stock solution was added to 20 ml test solution; for 200 µmol·l$^{-1}$ correspondingly less. In control experiments, corresponding amounts of pure ethanol were added to the test solution. Verapamil was dissolved in DMSO; calcium and magnesium withdrawal was done by giving EDTA.

Experiments on Isolated Cells by Means of the Patch-clamp Technique

For the experiments on the intact epithelium, new epithelium must be collected daily, which is time-consuming and costly. Hence, the aim is to perform a faster and more efficient screening by experiments on cell cultures in order to identify those substances with which the use on the intact epithelium and ultimately on the animal in vivo seems worthwhile. The patch-clamp technique allows for detailed insights into the modes of action of the test substances and a stringent verification of which ion species are transported is possible.

All patch-clamp experiments are carried out with the standard method, which has been specified in detail in multiple publications, (Stumpff, Strauss et al. 1997; Stumpff, Que et al. 1999; Stumpff, Boxberger et al. 2005; Stumpff, Bondzio et al. 2007; Stumpff, Martens et al. 2009; Stumpff, Georgi et al. 2011), the disclosure of which is hereby incorporated by reference into the present application.

For this purpose, borosilicate glass capillaries (Harvard Apparatus, Holliston, Mass., USA) are pulled out with a DMZ Universal Puller (Zeitz-Instruments, Munich, Germany) to form a fine tip, which after being filled with the pipette solution (table 6) is placed onto the cells growing on a cover slip with the help of a micromanipulator, under microscopic control. The cells are first rinsed with a physiological saline solution (NaCl solution, table 7).

Applying a negative pressure achieves to induce a fusion of the lipid membrane of the cell with the glass wall of the capillary ("seal"). A further abrupt pressure pulse achieves to rupture the cell membrane located between the glass capillary and the cytosol in some of the cells in such a way that a connection between pipette and cytosol is established. The cell membrane here should continue to be kept closed with the edge of the pipette. The pipette solution can now flow into the cell.

With the help of the patch-clamp amplifier (HEKA Elektronic, Lambrecht, Germany) it is now possible to apply voltage pulses between a chlorinated silver wire located in the pipette and an earthed connection located in the bath outside of the cell, and to measure the induced currents across the cell membrane. Here, the pulse generation, data recording, capacitance compensation, filtering of data and data analysis takes place automatically by means of TIDA for Windows (HEKA Elektronic, Lambrecht, Germany). In particular, in this way it is possible to create a current-voltage curve for the examined cell for each point in time of the measurement, from which one can find out which ions are to what extent allowed through the cell membrane.

The supply of solution into the perfusion chamber with the cells takes place by means of two identical pumps (MS/CA4/840, Ismatec, Glattbrugg-Zürich, Switzerland), which were equipped with precision tubes (Tygon, Ismatec) to guarantee identical flow rates (4 ml·min$^{-1}$). All the eight tubes are inserted by means of a Milli-manifold (ALA Scientific Instruments, Westbury, N.Y., USA) into a heating cannula, with which the regulation of the temperature of the solutions to any kind of value (normally 37° C.) is made possible by means of a temperature controller (PH01, multichannel systems, Reutlingen, Germany). By means of intermediary three-way valves the setup makes rapid and smooth solution changes possible.

Example 1

TRP Modulators Influence the Conductivity of Intact Rumen Epithelium for Cations After clamping the epithelium, it is first rinsed on both sides with the buffer without ammonium pH 7.4 (table 2). Typically, one can already observe a discrete transepithelial current now, corresponding to the basic activity of the epithelial sodium pump (Na$^+$/K$^+$-ATPase). Where applicable, the microelectrode is now pierced into the epithelium if the simultaneous registration of intracellular parameters is required or desired. When the puncture is successful, a considerably negative potential (−20 mV to −40 mV) should set in.

On the apical side, a buffer containing ammonium is now applied (10 mM or 40 mM) pH 6.4 (table 4 and 5); the buffer of the basolateral side ("blood") remains unchanged. The pH-gradient setting in corresponds roughly to the physiological conditions in the rumen. One observes an increase in the transepithelial current or the transepithelial voltage, respectively, corresponding to a transport of the charged ion (see FIGS. 1 and 2).

Subsequently, the test substance can be added to the apical buffer in the desired amount. With the addition of the TRP channel agonist menthol (200 µmol·l$^{-1}$ to 1 mmol·l$^{-1}$) to the solution containing ammonium, one observes a further considerable rise in the transepithelial current or the transepithelial voltage, respectively, corresponding to an increased transport of the ammonium ion (NH$_4^+$) through the epithelium. With the addition of verapamil (1 mmol·l$^{-1}$), the current drops. Calcium withdrawal equally leads to an increase in the current. Altogether, these observations suggest a joint absorption path for ammonium and calcium through nonselective cation channels, the permeability of which can be modulated by various substances (e.g. menthol) (Vriens, Nilius et al. 2008; Nilius and Owsianik 2011).

The experiments in the Ussing chamber explained above were continued and likewise carried out with further exemplary TRP agonists and/or antagonists.

Effect of Ammonium on the Short-circuit Current

In FIG. 7A and table 14 below, one can see a current induced by adding ammonium, which said current is subsequently modulated by corresponding agonists.

TABLE 14

Statistical evaluation of experiments as in FIG. 7A; abbreviations here and in subsequent tables: n.s.—not significant; MV—mean value, SEM—standard error of the mean.

| | | | µA · cm$^{-2}$ | | | | normally | | |
|---|---|---|---|---|---|---|---|---|---|
| No. | Solution | n | MV | SEM | Median | 25% | 75% | distributed | p vs 1 | p vs 3 |
| 1 | NaCl | 37 | −2.43 | 2.28 | −3.60 | −11.48 | 2.40 | no | | n.s. |
| 2 | 40 mM NH$_4^+$ | 37 | −25.73 | 2.14 | −22.32 | −34.23 | −16.76 | | <0.05 | <0.05 |
| 3 | NaCl (w) | 35 | −2.68 | 1.95 | −5.19 | −9.03 | 2.27 | | n.s. | |

Dose Dependence of the Effect of Menthol

The effect of menthol on the short-circuit current through the rumen epithelium—corresponding to an increased transport of cations—was already explained above. Below, the results will be examined with respect to the dependence of the response of the current on the substance dose (see FIG. 7B and table 15).

TABLE 15

Dose dependence of the effect of menthol

| | | | μA · cm$^{-2}$ | | | | Normally | | |
|---|---|---|---|---|---|---|---|---|---|
| No. | Solution | n | MV | SEM | Median | 25% | 75% | distributed | p vs 1 | p vs 3 |
| 1 | 40 mM NH$_4^+$ | 11 | −30.99 | 3.70 | −30.65 | −39.00 | −22.40 | yes | | 0.02 |
| 2 | 200 μM menthol | 11 | −36.34 | 3.66 | −34.21 | −46.51 | −25.74 | | 0.01 | <0.001 |
| 3 | 40 mM NH$_4^+$ (w) | 11 | −26.42 | 2.71 | −25.70 | −35.09 | −19.19 | | 0.02 | |
| 1 | 40 mM NH$_4^+$ | 12 | −24.20 | 4.51 | −22.76 | −26.99 | −14.71 | yes | | 0.09 |
| 2 | 1 mM menthol | 12 | −28.73 | 4.83 | −26.90 | −34.76 | −18.14 | | 0.02 | 0.00 |
| 3 | 40 mM NH$_4^+$ (w) | 12 | −20.88 | 3.68 | −19.61 | −27.00 | −16.96 | | 0.09 | |

Effect of Cinnamaldehyde

With cinnamaldehyde there is a further active substance influencing the transport across the rumen epithelium, this time with an inhibiting profile (see FIG. 8A and table 16 below). Inhibiting the ammonium efflux from the rumen could lead to an increased integration of nitrogen into microbial protein and thereby reduce the excretion of nitrogen into the environment. A simultaneous inhibition of the calcium and proton resorption cannot be ruled out. Further in vitro experiments are necessary here. A sufficient supply with calcium and a sparing administration of concentrated feed could be a prerequisite for employment.

TABLE 16

Summary of the measurements with cinnamaldehyde

| | | | μA · cm$^{-2}$ | | | | Normally | | |
|---|---|---|---|---|---|---|---|---|---|
| No. | Solution | n | MV | SEM | Median | 25% | 75% | distributed | p vs 1 | p vs 3 |
| 1 | 40 mM NH$_4^+$ | 7 | −31.53 | 3.15 | −26.52 | −39.66 | −23.39 | yes | (p = 0.313) | |
| 2 | Cinnamaldehyde | 7 | −28.39 | 3.26 | −24.03 | −33.10 | −21.07 | | | |
| 3 | 40 mM NH$_4^+$ (w) | 7 | −28.30 | 4.81 | −27.36 | −35.79 | −23.22 | | | |

Effect of Methyl Salicylate

Methyl salicylate has an equally inhibiting profile with an inhibiting effect on the nitrogen resorption from the rumen. With such an indication, the focus should here also be on improving the protein utilization while reducing the nitrogen excretion. On average, the addition led to a maximum reduction of the transepithelial current of −25.44±1.8 μA·cm$^{-2}$ to −21.06±2.97 μA·cm$^{-2}$. With n=4, this reduction was not (yet) significant, but the trend is clear.

Effect of Thymol

In thymol, what is noticeable is the duration of the achieved inhibition, which can still be verified after washing out (see FIG. 9 and table 17 below). This substance should therefore be particularly applicable for inhibiting the ammonium resorption.

TABLE 17

Thymol leads to a long-term inhibition of the ammonium resorption

| | | | μA · cm$^{-2}$ | | | | Normally | | |
|---|---|---|---|---|---|---|---|---|---|
| No. | Solution | n | MV | SEM | Median | 25% | 75% | distributed | p vs 1 | p vs 3 |
| 1 | 40 mM NH$_4^+$ | 4 | −22.47 | 3.87 | −19.30 | −26.70 | −18.23 | yes | (p = 0.498) | |
| 2 | 100 μM thymol | 4 | −22.19 | 4.00 | −19.35 | −27.37 | −17.01 | | | |
| 3 | 40 mM NH$_4^+$ (w) | 4 | −15.82 | 9.60 | −20.91 | −29.01 | −2.63 | | | |

Example 2

TRP Modulators Influence the Conductivity of Isolated Rumen Cells for Cations

At the beginning of the experiment, the cells filled with the pipette solution containing sodium gluconate (table 6) are located in a bath solution containing NaCl (table 7). The current-voltage curve shows a profile rectifying outwards, with a negative reversal potential, corresponding to a high conductivity of the cell for chloride (=anion channel (Stumpff, Martens et al. 2009)) with a low basic conductivity for sodium (Leonhard-Marek, Stumpff et al. 2005). When the bath perfusion is now switched to a solution containing mainly ammonium as cation (table 8), one observes an increase in the current at a negative pipette potential, corresponding to an influx of the ammonium ion (NH$_4^+$).

In this context, it shall be pointed out once again that the measurements with the patch-clamp technique are meant to enable a faster "screening" of candidates for the experiments on the intact epithelium, hence, they can be carried out additionally as a pre-screening but are not essential for the screening method according to an aspect of the invention (see also section "Experiments on isolated cells by means of the patch-clamp technique" above).

Example 3

Feeding Feeds Containing TRP Modulators to Cattle

The candidate substances that were identified as the most promising in the in vitro experiments are administered to Holstein cattle, particularly to Holstein Friesian cows, according to randomized distribution with the standard diet. The cattle control group only receives the standard diet. The data collection takes place on the basis of the evaluation of performance and health parameters of the animals and data from the smaXtec Bolus (smaXtec animal care sales GmbH; Graz, AUSTRIA)).

As performance data, for example, the daily/weekly/monthly or yearly (305 days) milk yield per animal (in kilograms or liters) and the composition of the milk, e.g. with respect to the fat and protein content, are routinely registered and compared between the animals of the two groups. Alternatively or additionally, the conventional functional features such as appearance, fertility, calving behavior, still births are compared.

As health parameters, for example, findings (e.g. type of pathogen), localization of the illness (e.g. mammary glands, feet etc.) and treatments are registered and compared between the two groups. In particular, diseases are observed here, their occurrence and progression being compared, which can potentially be traced back to a rumen acidosis, such as e.g. mastitis, endometritis and infectious hoof diseases.

Registration of the health parameters can take place by means of accepted veterinary medicine methods, such as they are known in professional circles and specified, for example, in "*Modern techniques for monitoring high producing dairy cows*", Cook et al, In practice 28 (2006); 598-603.

By employing the above-mentioned specific rumen bolus there is the possibility to automatically register data from the rumen at intervals of 10 minutes. Additionally, blood, urine and fecal samples of the animals are taken and examined (to evaluate the calcium level and the acid-base status, among other things).

Example 4

TRP Modulators Influence the Calcium Flux Across the Rumen Epithelium

For a direct verification of a modulation of the calcium transport across the rumen epithelium, a radioactive calcium isotope ($Ca^{45}$) was employed in further experiments. The measurements were carried out in conventional Ussing chambers without continuous perfusion. Herein, tissue of N=4 (cattle) was collected and n=85 epithelia were used therein.

The isotope was employed on the mucosal side (corresponding to the side on which the food is) and the emergence on the blood side was measured.

Dose-dependent Effect of Menthol on the Calcium Flux Across the Rumen Epithelium Approach: Three groups were formed. One group remained untreated as control. The other two groups were each treated with menthol at a dose of 200 µM or 1 mM, respectively, and compared to the control (100%). Herein, a concentration-dependent increase in the calcium transport across the rumen tissue was measured after the addition of menthol in two different concentrations compared to the control group.

Effect of Thymol on the Calcium Flux Across the Rumen Epithelium

Approach: First, a basal value of the Ca flux across the rumen epithelium was detected. Then a substance was added. The subsequently measured Ca flux was compared to the starting value (100%). In view of the inhibiting effect of thymol on the ammonium resorption from the rumen with a possible improvement of the nitrogen utilization, it was of interest to find out how this active substance influences the calcium resorption (see FIG. 10B for the results of the measurements). The results so far, however, indicate that there is no significant long-term reduction of the calcium transport, but instead that a trend to increase the calcium resorption is becoming visible.

Thus, the above results show that by employing specific TRP modulators (such as e.g. menthol) an increase in the calcium transport across the rumen epithelium can be induced.

APPENDIX

Composition of the Test Solutions Used

—Experiments on the Intact Epithelium—

TABLE 1

| Transport buffer | | |
| --- | --- | --- |
| Substance | mol/l | g/l |
| NaCl | 115.00 | 6.72 |
| $NaHCO_3$ | 25.00 | 2.100 |
| $NaH_2PO_4$ | 0.40 | 0.06 |
| $Na_2HPO_4$ | 2.40 | 0.43 |
| KCl | 5.00 | 0.37 |
| HEPES | 10.00 | 2.38 |
| $C_6H_{12}O_6 \cdot H_2O$ | 5.00 | 0.99 |
| $MgCl_2$ (1 mol/l) | 1.20 | 0.24 |
| $CaCl_2 \cdot 2\ H_2O$ | 1.20 | 0.18 |

Gassing: 95% $CO_2$/5% $O_2$, ad 300 mOsmol/l (mannitol); pH 7.4 (trizma base)

TABLE 2

| Buffer without ammonium pH 7.4 | | |
| --- | --- | --- |
| Substance | mol/l | g/l |
| NaCl | 70.00 | 4.09 |
| $NaH_2PO_4$ | 0.40 | 0.06 |
| $Na_2HPO_4$ | 2.40 | 0.43 |
| KCl | 5.00 | 0.37 |
| $C_6H_{12}O_6 \cdot H_2O$ | 5.00 | 0.99 |
| MOPS | 8.00 | 1.67 |
| Glutamine | 2.50 | 0.37 |
| Na gluconate | 30.00 | 6.544 |
| $MgCl_2$ (1 mol/l) | 1.20 | 0.24 |
| $CaCl_2 \cdot 2\ H2O$ | 1.20 | 0.18 |
| NMDGCl | 40.00 | 7.809 |

Gassing: 100% $O_2$, ad 300 mOsmol/l (mannitol); pH 7.4 (trizma base)

TABLE 3

| Buffer without ammonium pH 6.4 | | |
| --- | --- | --- |
| Substance | mol/l | g/l |
| NaCl | 70.00 | 4.09 |
| $NaH_2PO_4$ | 0.40 | 0.06 |

TABLE 3-continued

Buffer without ammonium pH 6.4

| Substance | mol/l | g/l |
|---|---|---|
| $Na_2HPO_4$ | 2.40 | 0.43 |
| KCl | 5.00 | 0.37 |
| $C_6H_{12}O_6 \cdot H_2O$ | 5.00 | 0.99 |
| MOPS | 8.00 | 1.67 |
| Glutamine | 2.50 | 0.37 |
| Na gluconate | 30.00 | 6.544 |
| $MgCl_2$ (1 mol/l) | 1.20 | 0.24 |
| $CaCl_2 \cdot 2\ H_2O$ | 1.20 | 0.18 |
| NMDGCl | 40.00 | 7.809 |

Gassing: 100% $O_2$, ad 300 mOsmol/l (mannitol); pH 6.4 (trizma base)

TABLE 4

Buffer containing ammonium pH 6.4 (10 mM)

| Substance | mol/l | g/l |
|---|---|---|
| NaCl | 70.00 | 4.09 |
| $NaH_2PO_4$ | 0.40 | 0.06 |
| $Na_2HPO_4$ | 2.40 | 0.43 |
| KCl | 5.00 | 0.37 |
| $C_6H_{12}O_6 \cdot H_2O$ | 5.00 | 0.99 |
| MOPS | 8.00 | 1.67 |
| Glutamine | 2.50 | 0.37 |
| Na gluconate | 30.00 | 6.544 |
| $MgCl_2$ (1 mol/l) | 1.20 | 0.24 |
| $CaCl_2 \cdot 2\ H_2O$ | 1.20 | 0.18 |
| $NH_4Cl$ | 10.00 | 0.534 |
| NMDGCl | 30.00 | 5.857 |

Gassing: 100% $O_2$, ad 300 mOsmol/l (mannitol); pH 6.4 (trizma base)

TABLE 5

Buffer containing ammonium pH 6.4 (40 mM)

| Substance | mol/l | g/l |
|---|---|---|
| NaCl | 70.00 | 4.09 |
| $NaH_2PO_4$ | 0.40 | 0.06 |
| $Na_2HPO_4$ | 2.40 | 0.43 |
| KCl | 5.00 | 0.37 |
| $C_6H_{12}O_6 \cdot H_2O$ | 5.00 | 0.99 |
| MOPS | 8.00 | 1.67 |
| Glutamine | 2.50 | 0.37 |
| Na gluconate | 30.00 | 6.544 |
| $MgCl_2$ | 1.20 | 0.24 |
| $CaCl_2 \cdot 2\ H_2O$ | 1.20 | 0.18 |
| $NH_4Cl$ | 40.00 | 2.138 |

Gassing: 100% $O_2$, ad 300 mOsmol/l (mannitol); pH 6.4 (trizma base)

—Experiments on Isolated Cells—

TABLE 6

Pipette solution

| Substance | mol/l | g/l |
|---|---|---|
| KCl | 5.00 | 0.37 |
| $NaH_2PO_4 \cdot H_2O$ | 1.00 | 0.14 |
| Na gluconate | 128.20 | 27.966 |
| Hepes | 10.00 | 2.38 |
| $CaCl_2 \cdot 2\ H_2O$ | 2.00 | 0.29 |
| $MgCl_2 \cdot 6\ H_2O$ | 1.10 | 0.22 |
| EGTA | 5.00 | 1.90 |
| NaCl | 8.80 | 0.514 |

No gassing, ad 290 mOsmol/l (mannitol); pH 7.2 (trizma base)

This solution is, where applicable, modified, should this be necessary for the signal transduction (e.g. addition of MgATP, reduction of EGTA, etc.)

TABLE 7

NaCl Solution

| Substance | mol/l | g/l |
|---|---|---|
| KCl | 5.00 | 0.37 |
| $NaH_2PO_4 \cdot H_2O$ | 1.00 | 0.14 |
| NaCl | 137.00 | 8.006 |
| Hepes | 10.00 | 2.38 |
| $CaCl_2 \cdot 2\ H_2O$ | 1.70 | 0.25 |
| $MgCl_2 \cdot 6\ H_2O$ | 0.90 | 0.18 |

No gassing, ad 290 mOsmol/l (mannitol); pH 7.4 (trizma base)

TABLE 8

NH4Cl Solution

| Substance | mol/l | g/l |
|---|---|---|
| $NH_4Cl$ | 130.00 | 6.95 |
| $NaH_2PO_4 \cdot H_2O$ | 1.00 | 0.14 |
| NaCl | 5.00 | 0.292 |
| HEPES | 10.00 | 2.38 |
| $CaCl_2 \cdot 2\ H_2O$ | 1.70 | 0.25 |
| $MgCl_2 \cdot 6\ H_2O$ | 0.90 | 0.18 |

No gassing, ad 290 mOsmol/l (mannitol); pH 7.4 (trizma base)

—Feed Composition—

TABLE 9

Exemplary composition of a commercially available concentrated (cattle) feed
Feed component [g/kg dry matter]

| Crude ash | 70 |
|---|---|
| Crude protein | 200 |
| Crude fibre | 100 |
| Calcium | 9 |
| Phosphate | 7 |
| Magnesium | 4 |
| Potassium | 12 |
| Sodium | 3.5 |
| Chloride | 5.5 |
| Sulfur | 1.5 |

—Substances Modulating TRP Channels—

TABLE 10

TRPV modulators

| Substance | Effect |
|---|---|
| TRPV1 | |
| Capsaicin | Agonist |
| Piperine | Agonist |
| Eugenol | Agonist |
| Resiniferatoxin | Agonist |
| Gingerol | Agonist |
| Vanillylacetone | Agonist |
| Evodiamine | Agonist |
| Cannabidiol | Agonist |
| Polygodial | Agonist |
| Isovelleral | Agonist |
| Camphor | Agonist |
| Vanillotoxin 1, 2 and 3 | Agonist |
| Thapsigargin | Antagonist |
| Olvanil | Agonist |

TABLE 10-continued

TRPV modulators

| Substance | Effect | |
|---|---|---|
| Capsazepine | Antagonist | |
| Cannabidiol | Agonist | |
| TRPV2 | | |
| Tetrahydrocannabinol | Agonist | |
| TRPV3 | | |
| Carvacrol | Agonist | |
| Eugenol | nonspecific | |
| Thymol | nonspecific | |
| Camphor | nonspecific | |
| Vanillin | | |
| Menthol | nonspecific | |
| TRPV4 | | |
| Bisandrographolide A | Agonist | |

TABLE 11

TRPM modulators

| Substance | Effect | |
|---|---|---|
| TRPM8 | | |
| Menthol | Agonist | |
| Eucalyptol | Agonist | |
| Menthone | Agonist | |
| Geraniol | Agonist | |
| Linalool | Agonist | |
| Menthyl lactate | Agonist | |
| Cis- and trans-p-menthane-3,8-diol | Agonist | |
| L-carvone | Agonist | |
| Isopulegol | Agonist | |
| Hydroxyl-citronellal | Agonist | |
| Eugenol | Agonist | But also TRPA1 and TRPV1 |
| Cinnamaldehyde | Antagonist | Antagonist |
| Ethanol | Antagonist | Inhibited by modulation of the PiP2-interaction |
| Icilin | Agonist | |
| Menthone | Agonist | |

TABLE 12

TRPA modulators

| Substance | Effect | |
|---|---|---|
| TRPA1 | | |
| Allyl isothiocyanate | Agonist | |
| Benzyl isothiocyanate | Agonist | |
| Phenylethyl isothiocyanate | Agonist | |
| Isopropyl isothiocyanate | Agonist | |
| Methyl isothiocyanate | Agonist | |
| Cinnamaldehyde | Agonist | |
| Eugenol | Agonist | But also TRPM8 and TRPV1 |
| Gingerol | Agonist | |
| Methyl saliciate | Agonist | |
| Allicin | Agonist | But also TRPV1 |
| Carvacrol | Agonist | |
| Camphor | Antagonist | |
| Menthol | Antagonist | But activates TRPM8 |

TABLE 12-continued

TRPA modulators

| Substance | Effect |
|---|---|
| Tetrahydrocannabinol | Agonist |
| Wasabi, mustard oil | Agonist |
| Yellow mustard | Agonist |

TABLE 13

Nonspecific modulators
Nonspecifically effective (activating a row of TRP channels, the TRPV3 among them)
Piperidine
Bisandrographolide
Icilin
Verapamil
Quinidin
GsMTx4
*Hypericum perforatum* (St. John's wort)
Hyperforin
Capsiate
Vanillylacetone (zingerone)
Evodiamine
Menthyl salicilate
Mustard oil
Ginsenoside
Carveol
Paradol
Resiniferanoids
Capsiate
Other Capsaicinoids
*Zingiber officinale*
Vanillylacetone (zingerone)
Evodiamine
[6,8,10]Shogaol
Other shogaols
*Cannabis*
Tetrahydrocannabinol
Cannabidiol
Other Cannabinoids
Drimanial
Cinnamodial
Cinnamosmolide
Cinnamolide
Afromodial
Ancistrodial
Merulidial
Drimenol
Grifolin
Neogrifolin
Albaconol
Prenylphenol
BCTC (N(4Tertiarybutylphenyl)4(3cholorphyridin2yl)tetrahydro-pyrazin 1(2H)carboxamide
Isovelleral
Vanillotoxin 1, 2 and 3
Arvanil
Cnidarian envenomations
Thapsigargin
Yohimbine
AG489 toxin
AG505 toxin
Paradol
Allyl isothiocyanate
Geraniol
Linalool
Menthyl lactate
Cis- and trans-p-menthane-3,8-diol
L-carvone
Isopulegol
Hydroxyl-citronellal
Borneol
Prostaglandin
Prostaglandin synthesis inhibitors
Acetylsalicylic acid TABLE 13-continued

| Nonspecific modulators Nonspecifically effective |
| --- |
| Paracetamol |
| Ibuprofen |

LITERATURE

[1] De Campeneere S, De Boever J L, Vanacker J M, Messens W, De Brabander D L: Feeding measures to reduce nitrogen excretion in dairy cattle. *Arch Anim Nutr* 2009, 63(2):87-103.

[2] Vanhatalo A, Kuoppala K, Ahvenjarvi S, Rinne M: Effects of feeding grass or red clever silage cut at two maturity stages in dairy cows. 1. Nitrogen metabolism and supply of amino acids. *J Dairy Sci* 2009, 92(11):5620-5633.

[3] Remond D, Bernard L, Savary-Auzeloux I, Noziere P: Partitioning of nutrient net fluxes across the portal-drained viscera in sheep fed twice daily: effect of dietary protein degradability. *Br J Nutr* 2009:1-12.

[4] Abdoun K, Stumpff F, Martens H: Ammonia and urea transport across the rumen epithelium: a review. *Anim Health Res Rev* 2006, 7(1-2):43-59.

[5] Harmeyer J, Martens H: Aspects of urea metabolism in ruminants with reference to the goat. *J Dairy Sci* 1980, 63(10):1707-1728.

[6] McDonald I W: The absorption of ammonia from the rumen of the sheep. *Biochem J* 1948, 42(4):584-587.

[7] bpb.de/gesellschaft/umwelt/dossier-umwelt/61246/luft-verschmutzung

[8] Gärtner K, Decker P, Hili H: Untersuchungen über die Passage von Harnstoff and Ammoniak durch die Pansenwand von Ziegen. *Pflugers Arch* 1961, 274:281-288.

[9] Abdoun K, Stumpff F, Wolf K, Martens H: Modulation of electroneutral Na transport in sheep rumen epithelium by luminal ammonia. *Am J Physiol* 2005, 289(3):G508-520.

[10] Stumpff F: Ionic Conductances of the Ruminal Epithelium. Freie Universität Berlin, Habil., Institut für Veterinär-Physiologie; 2010.

Galfi, P., S. Neogrady, et al. (1981). "Culture of epithelial cells from bovine ruminal mucosa." *Vet Res Commun* 4(4): 295-300.

Stumpff, F., O. Strauss, et al. (1997). "Characterization of maxi-K-channels in bovine trabecular meshwork and their activation by cyclic guanosine monophosphate." *Invest Ophthalmol Vis Sci* 38(9): 1883-1892.

Schweigel, M., I. Lang, et al. (1999). "Mg(2+) transport in sheep rumen epithelium: evidence for an electrodiffusive uptake mechanism." *Am J Physiol* 277(5 Pt 1): G976-982.

Stumpff, F., Y. Que, et al. (1999). "Stimulation of maxi-K channels in trabecular meshwork by tyrosine kinase inhibitors." *Invest Ophthalmol Vis Sci* 40(7): 1404-1417.

Abdoun, K., F. Stumpff, et al. (2005). "Modulation of electroneutral Na transport in sheep rumen epithelium by luminal ammonia." *Am J Physiol* 289(3): G508-520.

Leonhard-Marek, S., F. Stumpff, et al. (2005). "Basolateral Mg2+/Na+ exchange regulates apical nonselective cation channel in sheep rumen epithelium via cytosolic Mg2+." *Am J Physiol* 288(4): G630-645.

Stumpff, F., M. Boxberger, et al. (2005). "Stimulation of cannabinoid (CB1) and prostanoid (EP2) receptors opens BKCa channels and relaxes ocular trabecular meshwork." *Exp Eye Res* 80(5): 697-708.

Stumpff, F. and H. Martens (2006). A role for magnesium in the regulation of ruminal sodium transport. *Focus on signal transduction research*. G. McAlpine. New York, New Nova Science Publishers, Inc. (ISBN 13 978-1-60021-376-2): 37-66.

Stumpff, F., A. Bondzio, et al. (2007). "Effects of the *Bacillus thuringiensis* toxin Cry1Ab on membrane currents of isolated cells of the ruminal epithelium." *J Membr Biol* 219(1-3): 37-47.

Vriens, J., B. Nilius, et al. (2008). "Herbal compounds and toxins modulating TRP channels." *Curr Neuropharmacol* 6(1): 79-96.

Schweigel, M., J. Kuzinski, et al. (2009). "Rumen epithelial cells adapt magnesium transport to high and low extracellular magnesium conditions." *Magnes Res* 22(3): 133-150.

Stumpff, F., H. Martens, et al. (2009). "Cultured ruminal epithelial cells express a large-conductance channel permeable to chloride, bicarbonate, and acetate." *Pflugers Arch* 457(5): 1003-1022.

Abdoun, K., F. Stumpff, et al. (2010). "Modulation of urea transport across sheep rumen epithelium in vitro by SCFA and CO2." *Am J Physiol* 298(2): G190-202.

Leonhard-Marek, S., F. Stumpff, et al. (2010). "Transport of cations and anions across forestomach epithelia: conclusions from in vitro studies." *Animal* 4: 1037-1056.

Nilius, B. and G. Owsianik (2011). "The transient receptor potential family of ion channels." *Genome Biol* 12(3): 218.

Strecker, K. (2011). Untersuchungen zur pH-Regulation am Blättermagenepithel des Schafes mit H+-sensitiven Mikroelektroden. F B Veterinärmedizin. Berlin, FU Berlin. 178 pages.

Stumpff, F., M. I. Georgi, et al. (2011). "Sheep rumen and omasum primary cultures and source epithelia: barrier function aligns with expression of tight junction proteins." *J Exp Biol* 214(Pt 17): 2871-2882.

Abdoun, K., F. Stumpff, et al. (2005). "Modulation of electroneutral Na transport in sheep rumen epithelium by luminal ammonia." *Am J Physiol* 289(3): G508-520.

Allen W M, Davies D C (1981), "Milk fever, hypomagnesaemia and the "downer cow" syndrome." *Br. Vet. J.* 137, 435-441.

Blum J W, Fischer J A (1974) "Ätiologie, Pathophysiologie und Prophylaxe der hypocalcämischen Gebärparese des Rindes—eine Übersicht." *Schweiz. Arch. Tierheik.* 116, 603-628.

Ducusin, R. J., Y. Uzuka, E. Satoh, M. Otani, M. Nishimura, S. Tanabe und T. Sarashina. (2003), "Effects of extracellular Ca2+ on phagocytosis and intracellular Ca2+ concentrations in polymorphonuclear leukocytes of postpartum dairy cows." *Res Vet Sci.* 75(1):27-32

Dirksen, G.; Gründer, H. D.; Stöber, M.; (2002), "Innere Medizin und Chirurgie des Rindes." Parey in Blackwell Verlag GmbH, Berlin-Wien.

Enemark, J. M.; Jorgensen, R. J.; Kristensen, N. B.; (2004) "An evaluation of parameters for the detection of subclinical rumen acidosis in dairy herds." *Vet Res Commun* 28, 687-709.

Fürll, M., Jäkel, L., Bauerfeld, J., Groppel, B. (1995): "Gebärpareseprophylaxe mit "Anionenrationen". Prakt. Tierarzt, Coll. Vet. XXVI, 31-34.

Garrett, E. F.; Pereira, M. N.; Nordlund, K. V.; Armentano, L. E.; Goodger, W. J.; Oetzel, G. R.; (1999) "Diagnostic Methods for the detection of subacute ruminal acidosis in dairy cows." *J Dairy Sci* 82, 1170-1178.

Gasteiner J, Fallast M, Rosenkranz S, Häusler J, Schneider K, Guggenberger T (2009): "Zum Einsatz einer intraruminalen pH-Datenmesseinheit mit kabelloser Datenübertragung bei Rindern unter verschiedenen Fütterungsbedingungen." *Wien Tierärzft Mschrift*; Vet. Med. Austria 96 (2009), 188-194.

Gelfert C C, Loeffler L M, Framer S, Engel M, Manner K, Staufenbiel R. (2010) "Comparison of the impact of different anionic salts on the acid-base status and calcium metabolism in non-lactating, non-pregnant dairy cows." *Vet J.* September; 185(3):305-9. Epub 2009 Aug. 25.

Goff, J. P., Horst, R. L., (1993), "Oral administration of calcium salts for treatment of hypocalcemia in cattle." *J. Dairy Sci.* 76, 101-108.

Goff, J. P., Brown, T. R., Stokes, S. R., Brawley, C. L., Valdez, F. R., (2002), "Titration of the proper dose of calcium propionate (NutroCAL) to be included in an oral drench for fresh cows." *J. Dairy Sci.* 85 (Suppl. 1), 189

Goff J P, Ruiz R, Horst R L. (2004) Relative acidifying activity of anionic salts commonly used to prevent milk fever. *J Dairy Sci. May;* 87(5):1245-55.

Horst, R. L. (1986), "Regulation of calcium and phosphorus homeostasis in the dairy cow", *Journal of Dairy Science* 69, 604-616

Horst, R. L., Goff, J. P. and Reinhardt, T. A., (1994), 'Calcium and vitamin D metabolism in the dairy cow', *Journal of Dairy Science* 77, pp. 1936-1951

Horst R L, Goff J P, Reinhardt T A, Buxton D R (1997), "Strategies for preventing milk fever in dairy cattle." *J. Dairy Sci.* 80, 1269-1280.

Houe, H., S. Ostergaard, T. Thilsing-Hansen, R. J. Jorgensen, T. Larsen, J. T. Sorensen, J. F. Agger and J. Y. Blom. (2001) "Milk fever and subclinical hypocalcaemia—an evaluation of parameters on incidence risk, diagnosis, risk factors and biological effects as input for a decision support system for disease control." *Acta Vet Scand.* 42(1):1-29

Joris Vriens, Bernd Nilius and Rudi Vennekens, (2008), "Herbal Compounds and Toxins Modulating TRP Channels" *Current Neuropharmacology* 6, 79-96 79

Kimura, K., T. A. Reinhardt und J. P. Goff. (2006) "Parturition and hypocalcemia blunts calcium signals in immune cells of dairy cattle" *J Dairy Sci.* 89(7):2588-2595

Kraft W, Dürr U M (2005) Klinische Labordiagnostik in der Tiermedizin. Schattauer Verlag, Stuttgart.

Lang, I. and H. Martens (1999). "Na transport in sheep rumen is modulated by voltage-dependent cation conductance in apical membrane." *Am J Physiol* 277(3 Pt 1): G609-618.

Littledike, E. T., G. W. Engstrom, and M. Sachs. (1986), "Methods for sequential sampling and analysis of renal 25-hydroxyvitamin D3 1-, 24, and 23-hydroxylase activities of dairy cows and calves injected with 1α-hydroxyvitamin D3." *J. Dairy Sci.* 69:990-997.

Malz, C., Meyer, C. (1992), "Neue Aspekte zur Pathogenese und Therapie der hypocalcämischen Gebärparese.", Prakt. Tierarzt 73, 507-515.

Martens, H. and J. Harmeyer (1978). "Magnesium transport by isolated rumen epithelium of sheep." *Res Vet Sci* 24(2): 161-168.

Martig J (2002), "Hypokalzämische Gebärlähmung" In: G. Dirksen; H. D. Gründer u. M. Stöber (Eds.): "Innere Medizin und Chirurgie des Rindes", 4. Ed. Blackwell Verlag Berlin, Wien, 1245-1254.

Nordlund K V and Garrett E F: "Rumenocentesis: a technique for collecting rumen fluid for the diagnosis of subacute rumen acidosis in dairy herds." *Bovine Practitioner* 1994, 28, 109-112.

Nordlund K V, Garrett E F, Oetzel G R: "Herd-based rumenocentesis—a clinical approach to the diagnosis of subacute rumen acidosis." Compend. contin. Educ. pract. Vet. 1995, 17, p. 48-56.

Oetzel G R (1988), "Parturient paresis and hypocalcemia in ruminant livestock." Vet. Clinics of North America: Food Anim. Pract. 4, 351-364.

Radostits O M, Gay C G, Blood D C, Hinchcliff K W (2000) Parturient paresis (milk fever). In: Radostits. O. M., Gay, C. G., Blood, D. C., Hinchcliff, K. W. Veterinary Medicine. A textbook of the diseases of cattle, sheep, pigs, goats and horses. 9th Ed. W.B. Saunders, London, 1420-1435.

Ramsey, I. S., M. Delling, et al. (2006). "An introduction to TRP channels." *Annual Review of* Physiology 68: 619-647.

Schweigel, M., I. Lang, et al. (1999). "Mg(2+) transport in sheep rumen epithelium: evidence for an electrodiffusive uptake mechanism." *Am J Physiol* 277(5 Pt 1): G976-982.

Smith, P. L., K. N. Maloney, et al. (2006). "Bisandrographolide from Andrographis *paniculata* activates TRPV4 channels." Journal of Biological Chemistry 281(40): 29897-29904.

Leonhard-Marek, S., F. Stumpff, et al. (2005). "Basolateral Mg2+/Na+ exchange regulates apical nonselective cation channel in sheep rumen epithelium via cytosolic Mg2+." *Am J Physiol* 288(4): G630-645.

Xu, H., M. Delling, et al. (2006). "Oregano, thyme and clove-derived flavors and skin sensitizers activate specific TRP channels." *Nat Neurosci* 9(5): 628-635.

The invention claimed is:

1. A method of improving gastrointestinal tract disorders the disorders to be improved being chosen from the group consisting of parturient paresis, grass tetany, rumen acidosis, Hoflund syndrome, systemic alkalosis, displaced abomasum, and laminitis, by modulation of a Transient Receptor Potential (TRP) channel in an animal from the suborder of the ruminants (Ruminantia) or the tylopods (Tylopoda) by a feed supplement containing at least one TRP agonist selected from the group consisting of allicin, allyl isothiocyanate, camphor, carvacrol, eucalyptol, geraniol, gingerol, hydroxyl-citronellal, icilin, isopropyl isothiocyanate, isopulegol, isovelleral, L-carvone, linalool, menthol, menthone, menthyl lactate, methyl salicylate, methyl isothiocyanate, mustard oil, olvanil, phenylethyl isothiocyanate, piperine, polygodial, thymol, vanillin, vanillotoxin 1, 2 or 3, vanillylacetone, and yellow mustard, and/or at least one TRP antagonist selected from the group consisting of borneol, cannabidiol, cannabis, capsazepine, carveol, drimenol, ginsenoside, grifolin, GsMTx4, merulidial, thapsigargin, and thymol.

2. The method according to claim 1, wherein the feed supplement contains at least one TRP agonist and/or at least one TRP antagonist for influencing the resorption of cations in the rumen.

3. The method according to claim 2, wherein the cations comprise ammonia and/or calcium.

4. The method according to claim 1, wherein the TRP agonist and/or the TRP antagonist is present as an isolated active substance in the feed supplement.

5. The method according to claim 1, wherein the TRP agonist is selected from the group consisting of menthol, menthone, eucalyptol, geraniol, and methyl salicylate.

6. The method according to claim 1, wherein the TRP agonist comprises menthol.

7. The method according to claim 1, wherein the TRP agonist and/or the TRP antagonist is employed in a concentration range of 0.01 to 10 g/kg feed.

8. The method according to claim 1, wherein the feed supplement contains at least two or more TRP agonists and/or TRP antagonists.

9. The method according to claim 1, wherein the gastrointestinal tract disorder comprises rumen acidosis and/or parturient paresis.

10. A method of improving gastrointestinal tract disorders the disorders to be improved being chosen from the group consisting of parturient paresis, grass tetany, rumen acidosis, Hoflund syndrome, systemic alkalosis, displaced abomasum, and laminitis by a TRP agonist selected from the group consisting of allicin, allyl isothiocyanate, camphor, carvacrol, eucalyptol, geraniol, gingerol, hydroxyl-citronellal, icilin, isopropyl isothiocyanate, isopulegol, isovelleral, L-carvone, linalool, menthol, menthone, menthyl lactate, methyl salicylate, methyl isothiocyanate, mustard oil, olvanil, phenylethyl isothiocyanate, piperine, polygodial, thymol, vanillin, vanillotoxin 1, 2 or 3, vanillylacetone, and yellow mustard and/or a TRP antagonist selected from the group consisting of borneol, cannabidiol, cannabis, capsazepine, carveol, drimenol, ginsenoside, grifolin, GsMTx4, merulidial, thapsigargin, and thymol.

11. The method of claim 1, wherein improving the gastrointestinal tract disorders results in increased protein utilization and/or reduced nitrogen excretion by the treated animal.

12. The method according to claim 1, wherein the TRP antagonist comprises thymol.

* * * * *